United States Patent [19]
Flynn et al.

[11] Patent Number: 5,521,193
[45] Date of Patent: May 28, 1996

[54] BENZIMIDAZOLE COMPOUNDS

[75] Inventors: Daniel L. Flynn, Mundelein; Alan E. Moormann, Skokie; Daniel P. Becker, Glenview, all of Ill.; Michael S. Dappen, San Bruno, Calif.; Roger Nosal, Buffalo Grove, Ill.; Robert L. Shone, Palatine, Ill.; Clara I. Villamil, Glenview, Ill.

[73] Assignee: G. D. Searle & Co., Chicago, Ill.

[21] Appl. No.: 445,057

[22] Filed: May 19, 1995

Related U.S. Application Data

[60] Division of Ser. No. 325,303, Jun. 23, 1993, which is a continuation-in-part of Ser. No. 903,835, Jun. 24, 1992, Pat. No. 5,280,028.

[51] Int. Cl.$^6$ .................. A61K 31/395; C07D 221/02
[52] U.S. Cl. ................. 514/290; 514/294; 514/387; 546/79; 546/94; 548/305.1
[58] Field of Search ............ 546/79, 94; 514/294, 514/290, 387; 548/305.1

[56] References Cited

U.S. PATENT DOCUMENTS

| | | | |
|---|---|---|---|
| 4,083,985 | 4/1978 | Cohen et al. | 424/267 |
| 4,816,453 | 3/1989 | Watts | 514/217 |
| 5,300,512 | 4/1994 | Flynn et al. | 514/305 |

FOREIGN PATENT DOCUMENTS 0309423 9/1988 European Pat. Off. .

OTHER PUBLICATIONS

Schiantarelli et al. "The Prokinetic Properties of New Benzimidazolone Derivatives, etc." Pharmacological Research 22, Supp. 2 453 1990.
Dumuis et al. "Azabicycloalkyl benzimidazolone Derivatives etc." Naunyn–Schmiedeberg's Arch Pharmacol 343 245–251 1991.
Turconi et al. "Synthesis of a New Class of 2,3–Dihydro–2–oxo–1H–benzimidazole–1–carboxylic Acid Derivatives" J. Med. Chem. 33, No. 8 2101–2108 1990.
CA 120:107013e Nitrogen–containing . . . antagonists. King et al., p. 1165, 1994.
CA 120:245105n Preparation . . . antagonists. Flynn et al., p. 1052, 1994.

*Primary Examiner*—Joseph K. McKane
*Attorney, Agent, or Firm*—Cynthia S. Kovacevic; Roger A. Williams

[57] ABSTRACT

This invention relates to compounds useful in treating $HT_4$ and/or $HT_3$ mediated, conditions of the formula

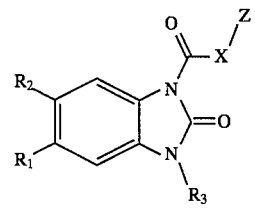

or a pharmaceutically acceptable salt thereof.

7 Claims, No Drawings

BENZIMIDAZOLE COMPOUNDS

This is a divisional application of co-pending application Ser. No. 08/325,303, filed on Jun. 23, 1993, still pending which is a continuation in part of application Ser. No. 07/903,835, filed Jun. 24, 1992, now issued as U.S. Pat. No. 5,280,028.

BACKGROUND OF THE INVENTION

The present invention relates to pharmaceutical agents (compounds) which act as $5\text{-}HT_4$ agonists or

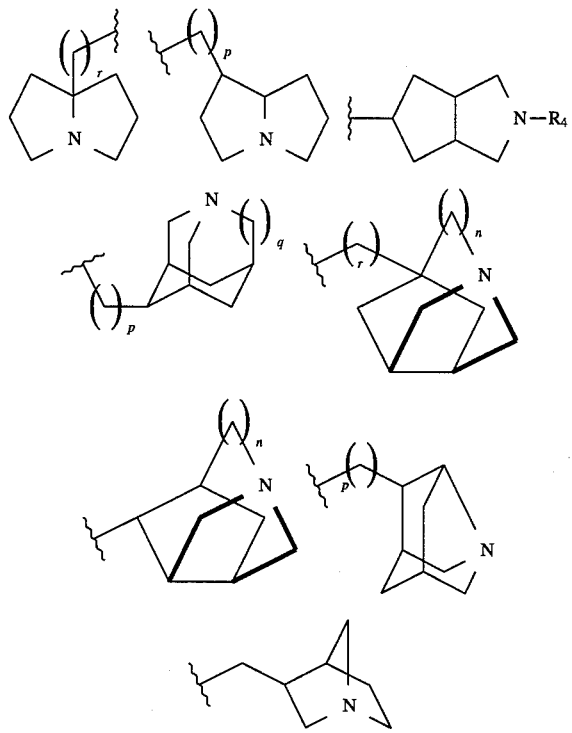

antagonists and/or $5\text{-}HT_3$ antagonists in mammals. As $5\text{-}HT_4$ agonists these agents are useful in the treatment of hypomotility disorders of the gastrointestinal (GI) tract including reflux esophagitis, non-ulcer dyspepsia, gastroparesis, ileus, irritable bowel syndrome (constipation predominant) and constipation. Additionally, $5\text{-}HT_4$ agonists are useful for the treatment of learning and memory disorders and as cardiovascular inotropic agents. As $5\text{-}HT_4$ antagonists these compounds are useful in the treatment of motility disorders of the GI tract such as diarrhea and irritable bowel syndrome (diarrhea predominant). As $5\text{-}HT_3$ antagonists these compounds are useful for treating emesis (caused by cancer chemotherapy or post-operative), anxiety, cognitive disorders, drug abuse either cravings or withdrawal syndrome) and irritable bowel syndrome (diarrhea predominant).

Serotonin (5-hydroxytryptamine; 5-HT) functions as a neurotransmitter in the mammalian central nervous system (CNS) and in the periphery. Serotonergic neurons regulate a wide variety of sensory, motor and cortical functions. Additionally serotonin regulates enteric reflexes, mediates contraction of the vascular smooth muscle and platelet shape change and aggregation and as such effects such diverse systems as the cardiovascular system and gastrointestinal system, in addition to the central nervous system.

Pharmacological and physiological studies show that the activity of serotonin is mediated by several distinct cell surface receptor subtypes. These receptor subtypes either transduce extracellular signals by activating GTP-binding proteins (G-protein-coupled receptor subtypes) or activate the opening of nonselective cation channels to promote fast, depolarizing responses in neurons (ligand-gated ion channel receptor subtypes). $5\text{-}HT_4$ belongs to the former category while $5\text{-}HT_3$ belongs to the latter. Agents which interact with these receptors thereby modulate a variety of ion channels and intracellular messenger signaling pathways thereby extending the flexibility of serotonin's activity and eliciting a multitude of cellular and physiological responses. P. Bonate, Clinical Neuropharmacology, Vol. 14, No. 1, pp. 1–16 (1991).

European Patent application 309,423 discloses azabicyclo substituted benzimidazoline-2-oxo-1-carboxylic acid derivatives which are useful as 5-HT receptor antagonists.

Dumuis et al., Nauyn-Schmiedeberg's Arch Pharmacol, (1991) 343:245–251 disclose azabicycloalkyl benzimidazolone derivatives as potent agonists at the $5\text{-}HT_4$ receptor.

In Pharmacological Research, Vol. 22, Supplement 2, (1990) Schiantarelli et al. disclose two benzimidazolone compounds useful as $5\text{-}HT_3$ antagonists and $5\text{-}HT_4$ agonists.

There is a need in the area of serotonin regulation for agents with broad clinical usefulness. Serotonin is one of the newer neurotransmitters to be recognized for physiological importance and agents which interact with 5-HT receptors are currently the focus of much research. P. Bonate, Clinical Neuropharmacology, Vol. 14, No. 1, pp. 1–16 (1991). Accordingly, it is the object of this invention to produce compounds for use as pharmaceutical agents which will exhibit $5\text{-}HT_4$ agonist or antagonist activity and/or $5\text{-}HT_3$ antagonist activity in mammals. The compounds of the present invention meet the need for an agent which has broad clinical usefulness for treating serotonin mediated conditions in mammals by administering a therapeutically effective amount of the compounds to act as $5\text{-}HT_4$ agonists or antagonists and/or $5\text{-}HT_3$ antagonists.

SUMMARY OF THE INVENTION

This invention relates to compounds of the Formula I

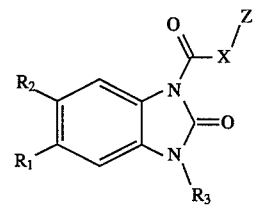

or a pharmaceutically acceptable salt thereof wherein $R_1$ and $R_2$ are independently selected from the group consisting of hydrogen, alkoxy, halogen, amino, monoalkylamino, dialkylamino, acylamino and alkylsulfonylamino;

$R_3$ is selected from the group consisting of H, alkyl and cycloalkyl;

X is NH or O;

Z is selected from the group consisting of

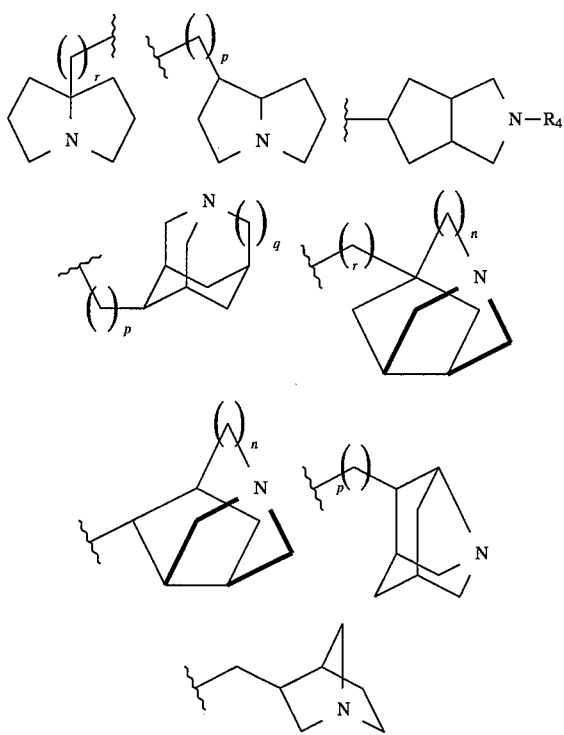

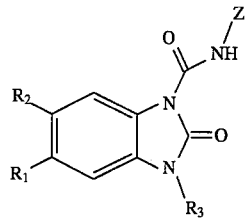

R₄ is alkyl, optionally substituted by cycloalkyl or phenyl;
n and r are independently 1 or 2;
p is 0 or 1; and
q is 0 or 1.

The present invention also provides pharmaceutical compositions comprised of a therapeutically effective amount of the compounds of Formula I in combination with a pharmaceutically acceptable carrier and a method for treating serotonin mediated conditions with said compositions which act as 5-HT$_4$ agonists or antagonists and/or 5-HT$_3$ antagonists.

DETAILED DESCRIPTION OF THE INVENTION

This invention encompasses compounds of the Formula I as previously described.

Within the class of compounds defined by Formula I, there is a sub-class of preferred compounds represented by Formula II:

$$\underset{R_1}{\underset{R_2}{\phantom{X}}}\begin{array}{c}\text{benzimidazolone with }O\text{=C-NH-Z on N, and }R_3\text{ on other N}\end{array}$$

or a pharmaceutically acceptable salt thereof
wherein R₁ and R₂ are independently selected from the group consisting of hydrogen, alkoxy, halogen, amino, monoalkylamino, dialkylamino, acylamino and alkylsulfonylamino;

R₃ is selected from the group consisting of H, alkyl and cycloalkyl;
Z is selected from the group consisting of

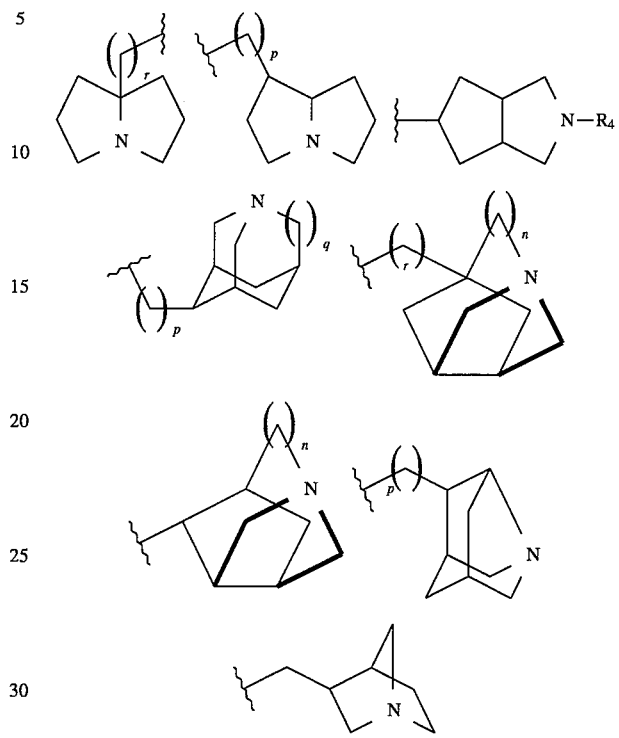

R₄ is alkyl, optionally substituted by cycloalkyl or phenyl;
n and r are independently 1 or 2;
p is 0 or 1; and
q is 0 or 1.

A more preferred subclass of compounds included within Formula II are:

endo-N-(1-azatricyclo[3.3.1.1$^{3,7}$]decan-4-yl)-3-ethyl-2,3-dihydro-2-oxo-1H-benzimidazole-1-carboxamide;

exo-N-(1-azatricyclo[3.3.1.1$^{3,7}$]decan-4-yl)-3-ethyl-2,3-dihydro 2-oxo-1H-benzimidazole-1-carboxamide;

endo-N-(1-azatricyclo[3.3.1.1$^{3,7}$]decan-4-yl)-6-chloro-2,3-dihydro 3-(1-methylethyl)-2-oxo-1H-benzimidazole-1-carboxamide;

endo-N-(1-azatricyclo[3.3.1.1$^{3,7}$]decan-4-yl)-5-chloro-2,3-dihydro 3-(1-methylethyl)-2-oxo-1H-benzimidazole-1-carboxamide;

endo-N-(1-azatricyclo[3.3.1.1$^{3,7}$]decan-4-yl)-6-chloro-3-ethyl-2,3-dihydro 2-oxo-1H-benzimidazole-1-carboxamide;

exo-N-(1-azatricyclo[3.3.1.1$^{3,7}$]decan-4-yl)-6-chloro-3-ethyl-2,3-dihydro 2-oxo-1H-benzimidazole-1-carboxamide;

endo-N-(1-azatricyclo[3.3.1.1$^{3,7}$]decan-4-yl)-5-chloro-3-ethyl-2,3-dihydro 2-oxo-1H-benzimidazole-1-carboxamide;

exo-N-(1-azatricyclo[3.3.1.1$^{3,7}$]decan-4-yl)-5-chloro-3-ethyl-2,3-dihydro 2-oxo-1H-benzimidazole-1-carboxamide;

cis-N-[(hexahydro-1H-pyrrolizin-1-yl)methyl]-2,3-dihydro-3-(1-methylethyl) 2-oxo-1H-benzimidazole-1-carboxamide;

5-chloro-N-[2-(hexahydro-7aH-pyrrolizin-7a-yl)ethyl]-2,3-dihydro-3-(1-methylethyl) 2-oxo-1H-benzimidazole-1-carboxamide;

N-[2-(hexahydro-7aH-pyrrolizin-7a-yl)ethyl]-2,3-dihydro-3-(1-methylethyl) 2-oxo-1H-benzimidazole-1-carboxamide;

N-[(hexahydro-7aH-pyrrolizin-7a-yl)methyl]-2,3-dihydro-3-(1-methylethyl) 2-oxo-1H-benzimidazole-1-carboxamide;

exo-N-(1-azatricyclo[3.3.1.1$^{3,7}$]decan-4-yl)-2,3-dihydro-3-(1-methylethyl) 2-xoo-1H-benzimidazole-1-carboxamide;

endo-N-(1-azatricyclo[3.3.1.1$^{3,7}$]decan-4-yl)-2,3-dihydro-3-(1-methylethyl) 2-oxo-1H-benzimidazole-1-carboxamide;

exo-N-(1-azatricyclo[3.3.1.1$^{3,7}$]decan-4-yl)-6-chloro-2,3-dihydro-3-(1-methylethyl) 2-oxo-1H-benzimidazole-1-carboxamide;

exo-N-(1-azatricyclo[3.3.1.1$^{3,7}$]decan-4-yl)-2,3-dihydro-3-(1-methylethyl) 2-oxo-1H-benzimidazole-1-carboxamide;

6-fluoro-N-[2-(hexahydro-7aH-pyrrolizin-7a-yl)ethyl]-2,3-dihydro-3-(1-methylethyl) 2-oxo-1H-benzimidazole-1-carboxamide;

N-[2-(hexahydro-7aH-pyrrolizin-7a-yl)ethyl]-2,3-dihydro-6-methoxy-3-(1-methylethyl) 2-oxo-1H-benzimidazole-1-carboxamide;

3-ethyl-N-[2-(hexahydro-7aH-pyrrolizin-7a-yl)ethyl]-2,3-dihydro 2-oxo-1H-benzimidazole-1-carboxamide;

N-(hexahydro-1H-2,5β-methano-3aα,6aα-cyclopenta[c]pyrrol-4α-yl)-2,3-dihydro-3-(1-methylethyl) 2-oxo-1H-benzimidazole-1-carboxamide;

6-Chloro-N-[2-(hexahydro-7aH-pyrrolizin-7a-yl)ethyl]-2,3-dihydro-3-(1-methylethyl) 2-oxo-1H-benzimidazole-1-carboxamide;

6-Chloro-5-amino-N-[2-(hexahydro-7aH-pyrrolizin-7a-yl)ethyl]-2,3-dihydro-3 (1-methylethyl)-2-oxo-1H-benzimidazole-1-carboxamide;

N-(exo-3-aza-3-methylbicyclo[3.3.0]octan-7-yl)-3-(1-methylethyl-2,3-dihydro 2-oxo-1H-benzimidazole-1-carboxamide;

N-(1-azatricyclo[3.3.1.1$^{3,7}$]decan-4-ylmethyl)-2,3-dihydro-3-(1-methylethyl) 2-oxo-1H-benzimidazole-1-carboxamide;

N-(1-azatricyclo[3.3.1.1$^{3,7}$]decan-4-ylmethyl)-6-chloro-2,3-dihydro-3-(1-methylethyl) 2-oxo-1H-benzimidazole-1-carboxamide;

N-[(Hexahydro-2β,6β-methano-1H, 7aα-pyrrolizin-1β-yl)methyl]-2,3-dihydro-3 (1-methylethyl)-2-oxo-1H-benzimidazole-1-carboxamide;

N-[(Hexahydro-2β,6β-methano-1H, 7aα-pyrrolizin-1α-yl)methyl]-2,3-dihydro-3 (1-methylethyl)-2-oxo-1H-benzimidazole-1-carboxamide;

N-[(Hexahydro-2β,6β-methano-1H, 7aα-pyrrolizin-1α-yl)-2,3-dihydro-3-(1-methylethyl 2-oxo-1H-benzimidazole-1-carboxamide;

N-[(Hexahydro-2β,6β-methano-1H, 7aα-pyrrolizin-1β-yl)-2,3-dihydro-3-(1-methylethyl 2-oxo-1H-benzimidazole-1-carboxamide;

N-(Hexahydro-2,6-methano-1H-pyrrolizin-1-ylmethyl)-2,3-dihydro-3-(1-methylethyl) 2-oxo-1H-benzimidazole-1-carboxamide;

N-[(Hexahydro-2,5β-methano-1H-3aα,6aα-cyclopenta[c]pyrrol-5-yl) methyl]-2,3-dihydro-3-(1-methylethyl)-2-oxo-1H-benzimidazole 1-carboxamide;

N-[(Hexahydro-2,5β-methano-1H-3aα,6aα-cyclopenta[c]pyrrol-5-yl) methyl]-6-chloro-2,3-dihydro-3-(1-methylethyl)-2-oxo-1H-benzimidazole 1-carboxamide;

N-[(endo-1-azabicyclo[2.2.1]heptan-3-yl)methyl-]-2,3-dihydro-3-(1-methylethyl) 2-oxo-1H-benzimidazole-1-carboxamide; and N-[(exo-1-azabicyclo[2.2.1]heptan-3-yl)methyl-]-2,3-dihydro-3-(1-methylethyl) 2-oxo-1H-benzimidazole-1-carboxamide.

Included within the classes and subclasses of compounds embraced by Formulas I–II are isomeric forms of the described compounds including diastereoisomers and enantiomers and tautomeric forms of the described compounds. Pharmaceutically acceptable salts of such compounds are also included as well as pharmaceutically acceptable salts of such isomers and tautomers.

In the structures herein a bond drawn across a bond in a ring indicates that the bond can be to any available atom of the ring structure.

The term "pharmaceutically acceptable salt," as used herein, refers to conventionally accepted pharmaceutical salts prepared by processes which are well known to those of ordinary skill in the art. [See for example, S. M. Berge, et al., "Pharmaceutical Salts," *J. Pharm. Sci.*, 66:1–19 (1977)].

The term "composition" as used herein means a product which results from the mixing or combining of more than one element or ingredient.

The term "pharmaceutically acceptable carrier" as used herein means a pharmaceutically-acceptable material, composition or vehicle, such as a liquid or solid filler, diluent, excipient, solvent or encapsulating material, involved in carrying or transporting a chemical agent from one organ or portion of the body to another organ or portion of the body.

The term "therapeutically effective amount" shall mean that amount of drug or pharmaceutical agent that will elicit the biological or medical response of a tissue, system or animal that is being sought by a researcher or clinician.

The term "alkyl" as used herein means a univalent hydrocarbon radical having from one to twelve carbon atoms, more preferably from one to six carbon atoms and derived by the removal of a single hydrogen atom from a straight or branched chain saturated hydrocarbon. Representative of such radicals are methyl, ethyl, n-propyl, isopropyl, n-butyl, sec.-butyl, isobutyl, tert-butyl, 2-ethylhexyl, n-octyl, and 2,4-dimethylphenyl.

The term "alkoxy" as used herein means an alkyl radical, as defined above having one or more oxygen atoms attached thereto. Representative alkoxy groups include methoxy, ethoxy, propoxy, and tert-butoxy.

The term halogen as used herein means a fluoro, chloro, bromo or iodo radical.

The term "monoalkylamino" as used herein is represented by the radical —$NHR_4$ wherein $R_4$ is an alkyl group as previously described.

The term "dialkylamino" as used herein is represented by the radical —$NR_4R_5$ wherein $R_4$ and $R_5$ are the same or different alkyl groups, as defined above.

The term "acylamino" as used herein is represented by the radical $$R_4-\overset{\overset{\displaystyle O}{\|}}{C}-NH-$$

wherein $R_4$ is an alkyl group as described above.

The term "alkylsulfonylamino" as used herein is represented by the radical $R_4$—$SO_2$—NH— wherein $R_4$ is an alkyl group as defined above.

The term "cycloalkyl" as used herein means an alicyclic radical with from 3 to 6 carbon atoms. Examples of suitable cycloalkyl radicals includes cyclopropyl, cyclopropenyl, cyclobutyl, cyclopentyl, cyclohexyl, and 2-cyclohexen-1-yl.

The compounds herein exhibit 5-$HT_4$ agonism or antagonism and/or 5-$HT_3$ antagonism. The 5-$HT_3$ antagonist activity possessed by the compounds of this invention was determined by the radioligand receptor binding assay as described herein and in the in vivo Bezold-Jarisch reflex procedure. 5-$HT_4$ agonist activity was determined in the in vitro rat tunice muscularis mucosae (TMM) assay. (Baxter et el., Naunyn Schmied Arch. Pharmacol, 1991, 343,439). The 5-$HT_4$ agonist or antagonist activity and/or 5-$HT_3$ antagonist activity of the compounds of the invention herein, can be determined by the assays as described herein, without undue experimention.

By virtue of their activity as 5-$HT_4$ agonists or antagonists and/or 5-$HT_3$ antagonists the compounds of Formula I and II are useful in treating serotonin mediated conditions such as gastrointestinal motility disorders, emesis, anxiety, cognitive disorders and other CNS disorders. As used herein 5-$HT_4$ agonist mediated conditions of the gastrointestinal tract include reflux esophagitis, non-ulcer dyspepsia, gastroparesis, ileus, irritable bowel syndrome (constipation predominant), and constipation. As used herein 5-$HT_4$ antagonist mediated conditions of the GI tract include diarrhea, and irritable bowel syndrome (diarrhea predominant). As used herein 5-$HT_3$ antagonist mediated conditions include emesis due to either cancer chemotherapy or postoperative, anxiety, cognitive disorders, drug abuse (either cravings or withdrawal syndrome), and irritable bowel syndrome (diarrhea predominant). A physician or veterinarian of ordinary skill can readily determine whether a subject exhibits such a serotonin mediated condition.

The compounds of the present invention can be administered in such oral dosage forms as tablets, capsules, softgels, pills, powders,, granules, elixirs or syrups. The compounds can also be administered intravascularly, intraperitoneally, subcutaneously, intramuscularly or topically using forms known to the pharmaceutical art. In general the preferred form of administration is oral.

For the orally administered pharmaceutical compositions and methods of the present invention, the foregoing active ingredients will typically be administered in admixture with suitable pharmaceutical diluents, excipients or carriers (collectively referred to hereinafter as "carrier" materials). Such carrier materials are suitably selected with respect to the intended form of administration and consistent with conventional pharmaceutical practices.

For example, for oral administration in the form of tablets or capsules, a therapeutically effective amount of one or more compounds of the present invention can be combined with any oral pharmaceutically acceptable inert carrier such as lactose, starch, sucrose, cellulose, magnesium stearate, and calcium sulfate or various combinations thereof. For oral administration in liquid forms, such as in softgels, elixirs, and syrups, a therapeutically effective amount of the active drug components can be combined with any oral pharmaceutically acceptable inert carrier such as water, ethanol, polyethylene glycol, vegetable oils, propylene glycol, and benzylalcohol or various combinations thereof.

When desired or necessary, suitable binders, lubricants, disintegrating agents, preservatives, and coloring or flavoring agents can also be incorporated into the mixture. Suitable binders include starch, gelatin, natural sugars, corn sweeteners, natural and synthetic gums and waxes, or combinations thereof. Lubricants can include boric acid, sodium benzoate, sodium acetate, and sodium chloride or combinations thereof. Visintegrators include without limitation starch, methylcellulose, agar, bentonite, and guar gum, or combinations thereof.

For intravascular, intraperitoneal, subcutaneous or intramuscular administration, one or more compounds of the present invention can be combined with a suitable carrier such as water, saline, and aqueous dextrose. For topical administration therapeutically effective amounts of one or more compounds of the present invention can be combined with pharmaceutically acceptable creams, oils, waxes, and gels.

Regardless of the route of administration selected, a therapeutically effective amount of the compounds of the present invention are formulated into pharmaceutically acceptable dosage forms by conventional methods known to those skilled in the art. The dosages for preventing or treating serotonin mediated conditions with the compounds of the present invention is determined in accordance with a variety of factors, including the type, age, weight, sex and medical condition of patient, the severity of the condition, the route of administration and the particular compound employed in the treatment. A physician or veterinarian of ordinary skill can readily determine and prescribe an effective amount of drug required to prevent or arrest progress of the condition. In so proceeding, the physician or veterinarian could employ relatively low doses at first and subsequently increase the dose until a maximum response is obtained. The daily doses of the compounds of the invention are ordinarily in the range of about 1 to 1000 mg, more preferably in the range of about 10 to 500 mg.

The compounds of this invention are generally prepared according to reaction schemes I and II.

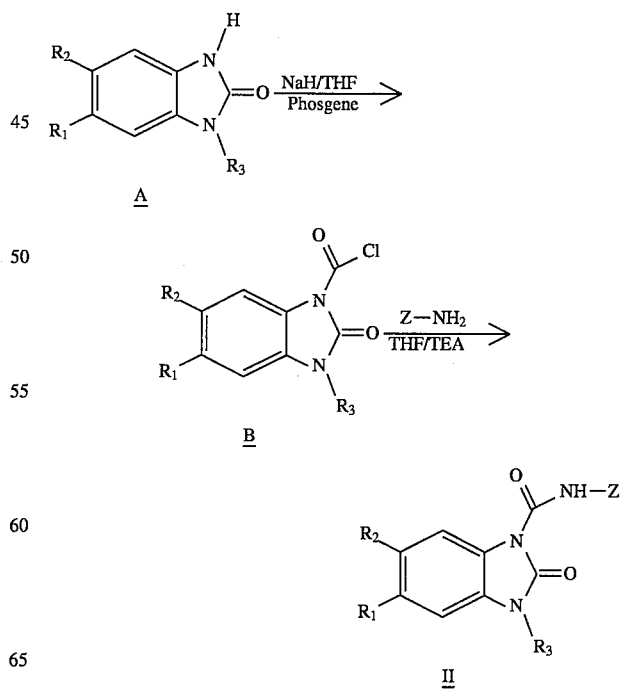

Scheme II

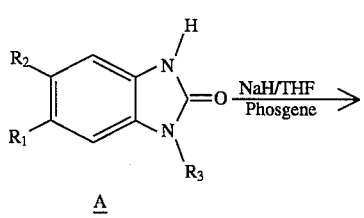

A

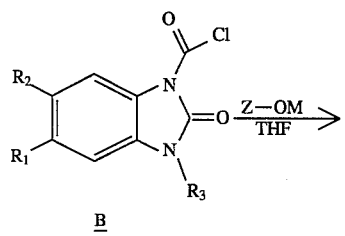

B

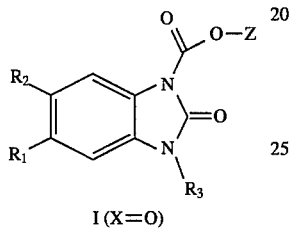

I (X=O)

As shown in reaction Scheme I the 3-unsubstituted benzimidazolones A are reacted with a base (preferably sodium hydride) in an inert etheral solvent (preferably tetrahydrofuran) to generate the sodium salt, which is reacted with phosgene to produce the 3-carbamoylchloride substituted benzimidazolone B. This intermediate is reacted with the appropriate amine (Z-NH$_2$, as defined above) in an inert solvent (preferably tetrahydrofuran) in the presence of a base (preferably triethylamine) to afford the desired compounds of formulae II.

Alternatively, as shown in reaction Scheme II, intermediate B is reacted with the appropriate alcohol (Z-OH, as defined above) or its metal salt (preferably Na, K, or Cs; formed by reaction with, by illustration, sodium hydride, potassium hydride, cesium carbonate) in an inert solvent (preferably tetrahydrofuran or dimethylformamide) at either ambient or elevated temperature (50° C. to 110° C.) to afford desired compounds of formulae I, wherein X=O.

The following examples illustrate the methods used to prepare the compounds of this invention. These examples are given by way of illustration only and are not meant to be construed as limiting the invention in spirit or scope, as many modifications in materials and methods will be apparent from this disclosure to one having ordinary skill in the art.

EXAMPLE 1

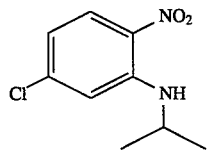

5-chloro-N-isopropyl-2-nitroaniline 5-chloro-2-nitroaniline (8.6 g; 0.05 mole), 2,2-dimethoxypropane (10.0 ml; 0.09 mole) and trifluoroacetic acid [TFA] (4.0 ml; 0.005 moles) were dissolved in toluene (100 ml) and stirred for 1 hr. A boron/pyridine complex (hereinafter BH$_3$ * pyridine) (5.0 ml; 0.05 moles) was added in 1.0 ml increments. The reaction was exothermic, and the reaction progress was monitored by tlc (40%EtOAc/hexane). Additional TFA, BH$_3$ * pyridine and 2,2-dimethoxypropane were added until the tlc indicated that the 5-chloro-2-nitroaniline was consumed. The reaction mixture was placed on a bed of silica and eluted with toluene. The product was the first major component to elute, which produced 6.6 g (61%) of a yellow crystalline solid.

$C_9H_{10}ClN_2O_2$ M.W. 213.63

| Elements | Calc | Found |
|---|---|---|
| Carbon | 50.36 | 50.27 |
| Hydrogen | 5.17 | 5.17 |
| Nitrogen | 13.05 | 12.97 |
| Chlorine | 16.52 | 15.92 |

EXAMPLE 2

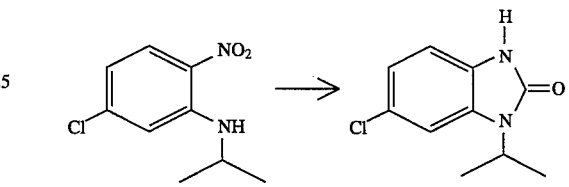

5-chloro-N-isopropyl-2-nitroaniline→6-chloro-1,3-dihydro-1 (1-methylethyl)-2H-benzimidazol-2-one 5-chloro-N-isopropyl-2-nitroaniline (6.5 g; 0.03 mole) was dissolved in MeOH (330 ml) and hydrogenated at room temperature, at 5.0 psi over Ra-Ni for 1.5 hr. at which time the theoretical hydrogen uptake had been achieved. The reaction mixture was filtered and the filtrate was concentrated. The residue was dissolved in CH$_2$Cl$_2$ (250 ml) and triphosgene (3.06 g; 0.01 mole) dissolved in 25 ml of CH$_2$Cl$_2$ was added. The reaction was exothermic. The reaction mixture was stirred for 1 hr. and then concentrated. The residue was placed on a bed of silica and eluted with EtOH/CH$_2$Cl$_2$ using a gradient from 5%→40% EtOH. The fractions containing the product were combined and concentrated to yield 2.7 g (43%) of a purple-white solid.

$C_{10}H_{11}ClN_2O$ M.W. 210.65

| Elements | Calc | Found |
|---|---|---|
| Carbon | 57.01 | 56.61 |
| Hydrogen | 5.26 | 5.29 |
| Nitrogen | 13.30 | 13.19 |
| Chlorine | 16.83 | 17.20 |

EXAMPLE 3

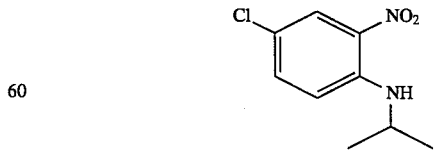

4-chloro-N-isopropyl-2-nitroaniline 4-chloro-2-nitroaniline (8.6 g; 0.05 mole), 2,2-dimethoxypropane (10.0 ml; 0.9 mole) and trifluoroacetic acid [TFA] (4.0 ml; 0.005 moles) were dissolved in toluene (100 ml) and stirred for 1 hr. BH₃ pyridine (5.0 ml; 0.05 moles) was added in 1.0 ml increments. The reaction was exothermic, and the reaction progress was monitored by tlc 40%EtOAc/Hexane. Additional TFA, BH₃ * pyridine and 2,2-dimethoxypropane were added until the tlc indicated that the 4-chloro-2-nitroaniline was consumed. The reaction mixture was placed on a bed of silica and eluted with toluene. The product was the first major component to elute, which produced 8.4 g (78%) of a yellow crystalline solid.

C₉H₁₀ClN₂O₂ M.W. 213.63

| Elements | Calc | Found |
| --- | --- | --- |
| Carbon | 50.36 | 50.44 |
| Hydrogen | 5.17 | 5.26 |
| Nitrogen | 13.05 | 12.96 |
| Chlorine | 16.52 | 16.22 |

EXAMPLE 4

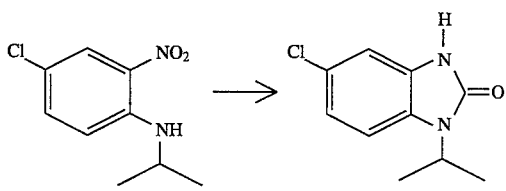

4-chloro-N-isopropyl-2-nitroaniline→5-chloro-1,3-dihydro-1 (1-methylethyl)-2H-benzimidazole-2-one 4-chloro-N-isopropyl-2-nitroaniline (8.3 g; 0.0389 mole) was dissolved in MeOH (330 ml) and hydrogenated at room temperature, at 5.0 psi over Ra-Ni for 1.5 hr. at which time the theoretical hydrogen uptake had been achieved. The reaction mixture was filtered and the filtrate was concentrated. The residue was dissolved in CH₂Cl₂ (250 ml) and triphosgene (3.9 g; 0.014 mole) dissolved in 25 ml of CH₂Cl₂ was added. The reaction was exothermic. The reaction mixture was stirred for 1 hr. and then concentrated. The solid was triturated with water and filtered, washed with Et₂O and suction dried which-produced 5.7 g (69.5%) of a purple-white solid.

C₁₀H₁₁ClN₂O M.W. 210.65

| Elements | Calc | Found |
| --- | --- | --- |
| Carbon | 57.01 | 56.89 |
| Hydrogen | 5.26 | 5.28 |
| Nitrogen | 13.30 | 13.29 |
| Chlorine | 16.83 | 16.54 |

EXAMPLE 4A

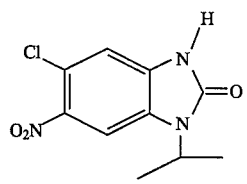

5-Chloro-6-nitro-1,3-dihydro-1-(1-methylethyl) 2H-benzimidazole-2-one

The compound of Example 4 (1.0 g, 5.0 mmol) was suspended in acetic anhydride (10 mL) and cooled in an ice bath. To this mixture was added dropwise 1.5 mL of a 1:2 mixture of nitric acid/acetic anhydride. The reaction mixture was stirred for 5 minutes before being poured into ice-water. The solid was filtered and washed well with water and suction-dried to afford 1.01 g (80%) of the title compound as a solid.

¹H NMR (300 MHz, DMSO-d6)δ1.49 (6H, d, J=12 Hz); 4.62 (1H, septet, J=12 Hz); 7.31 (1H, s); 8.0 (1H, s).

EXAMPLE 5

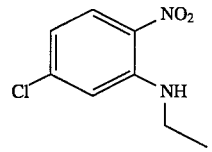

5-chloro-N-ethyl-2-nitroaniline 5-chloro-2-nitroaniline (17.2 g; 0.1 mole), acetalaldehyde diethyl acetal (Acetal) (21.1 ml; 0.15 mole) and TFA (7.7 ml; 0.1 moles) were dissolved in toluene (500 ml) and stirred for 1 hr. BH₃ * pyridine (10.0 ml; 0.1 moles) was added in 1.0 ml increments. The reaction was exothermic, and the reaction progress was monitored by tlc 40%EtOAc/Hexane. Additional TFA, BH₃ * pyridine and acetal were added until the tlc indicated that the 5-chloro-2-nitroaniline was consumed. The reaction mixture was washed 2X with water and placed on a bed of silica and eluted with toluene. The product was the first major component to elute. The product was crystallized from MeOH which produced 17.6 g (88%) of a yellow crystalline solid.

C₈H₉ClN₂O₂ M.W. 200.63

| Elements | Calc | Found |
| --- | --- | --- |
| Carbon | 47.89 | 47.69 |
| Hydrogen | 4.52 | 4.36 |
| Nitrogen | 13.96 | 13.92 |
| Chlorine | 17.67 | 17.71 |

EXAMPLE 6

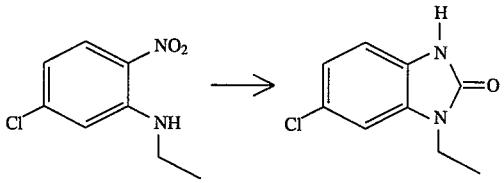

5-chloro-N-ethyl-2-nitroaniline→6-chloro-1-ethyl-1,3-dihydro 2H-benzimidazole-2-one 5-chloro-N-ethyl-2-nitroaniline (17.6 g; 0.0877 mole) was dissolved in MeOH (1.0 l) and hydrogenated at room temperature, at 5.0 psi over Ra-Ni for 1.9 hr. at which time the theoretical hydrogen uptake had been achieved. The reaction mixture was filtered and the filtrate was concentrated. The residue was dissolved in CH₂Cl₂ (500 ml) and triphosgene (8.6 g; 0.029 mole) dissolved in 50 ml of CH₂Cl₂ was added. The reaction was exothermic. The reaction mixture was stirred for 1 hr. and then concentrated. The solid was triturated with water and filtered, washed with Et₂O and suction dried which produced 7.9 g (46%) of a blue-white solid.

C₉H₉ClN₂O M. W. 196.64

| Elements | Calc | Found |
|---|---|---|
| Carbon | 52.57 | 52.18 |
| Hydrogen | 4.90 | 4.68 |
| Nitrogen | 13.62 | 13.68 |
| Chlorine | 17.24 | 17.17 |

EXAMPLE 7

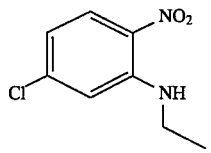

4-chloro-N-ethyl-2-nitroaniline 4-chloro-2-nitroaniline (8.6 g; 0.05 mole), acetaldehyde (5.5 ml; 0.05 mole) and HOAc (4.0 ml; 0.1 moles) were dissolved in toluene (100 ml) and stirred for 1 hr. $BH_3$ * pyridine (5.0 ml; 0.01 moles) was added in 1.0 ml increments. The reaction was exothermic, and the reaction progress was monitored by tlc (40%EtOAc/Hexane). Additional TFA, $BH_3$ * pyridine and acetaldehyde were added until the tlc indicated that the 4-chloro-2-nitroaniline was consumed. The reaction mixture was washed 2X with water and placed on a bed of silica and eluted with 20% EtOAc/Hexane. The product was the first major component to elute. The product was crystallized from MeOH which produced 5.0 g (50%) of a yellow crystalline solid.

$C_8H_9ClN_2O_2$ M.W. 200.63

| Elements | Calc | Found |
|---|---|---|
| Carbon | 47.89 | 47.57 |
| Hydrogen | 4.52 | 4.41 |
| Nitrogen | 13.96 | 14.07 |
| Chlorine | 17.67 | 17.77 |

EXAMPLE 8

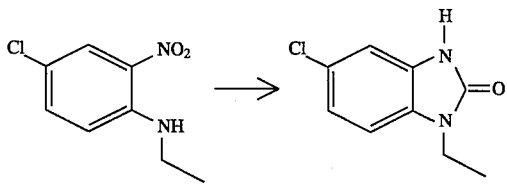

4-chloro-N-ethyl-2-nitroaniline→5-chloro-1-ethyl-1,3-dihydro 2H-benzimidazol-2-one 4-chloro-N-ethyl-2-nitroaniline (8.7 g; 0.0436 mole) was dissolved in MeOH (330 ml) and hydrogenated at room temperature, at 5.0 psi over Ra-Ni for 3.1 hr. at which time the theoretical hydrogen uptake had been achieved. The reaction mixture was filtered and the filtrate was concentrated. The residue was dissolved in $CH_2Cl_2$ (200 ml) and triphosgene (4.3 g; 0.0145 mole) dissolved in 25 ml of $CH_2Cl_2$ was added. The reaction was exothermic. The reaction mixture was stirred for 1 hr. then concentrated. The solid was triturated with water and filtered, washed with $Et_2O$ and suction dried which produced 5.5 g (64%) of a blue-white solid.

$C_9H_9ClN_2O$ M.W. 196.64

| Elements | Calc | Found |
|---|---|---|
| Carbon | 52.57 | 52.83 |
| Hydrogen | 4.90 | 4.90 |
| Nitrogen | 13.62 | 13.74 |
| Chlorine | 17.24 | 17.21 |

EXAMPLE 9

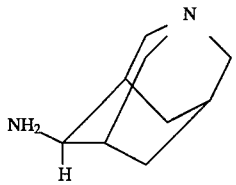

This compound was prepared by the methodology of E. A. Watts, in U.S. Pat. No. 4,816,453 (1989).

EXAMPLE 10

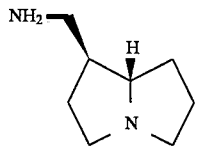

This compound was prepared by the method of D. L. Flynn et al., J. Med. Chem., 35, 1486 (1992).

EXAMPLE 11

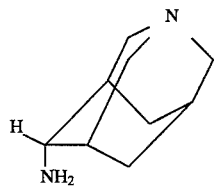

This compound was prepared by the methodology of E. A. Watts, in U.S. Pat. No. 4,816,453 (1989).

EXAMPLE 11A

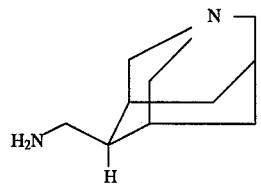

A solution of 923 mg (6.1 mmol) of 1-azaadamantane-4-one and 1.542 g (7.9 mmol) of tosylmethyl isocyanide in 21 ml of dry dimethoxyethane and 0.62 ml of absolute ethanol was cooled to −10° C. (ice-methanol). Potassium t-butoxide, 1.63 g (14.5 mmol), was added as a solid in five portions over 15 minutes. The reaction mixture was warmed to room temperature, stirred for two hours and was warmed to 40° C. for 15 min. The reaction mixture was filtered to remove precipitated solids and the filtrate was concentrated to provide an oil. The oil was dissolved in 7 ml of water, saturated with NaCl and extracted five times with 15 ml portions of ether. The ether extracts were dried over magnesium sulfate (MgSO₄), filtered and the ether evaporated to give 1.01 g of crude nitrile. Purification by low pressure chromatography on silica gel (4% MeOH/NH₃—CHCl₃) gave 0.38 g (38%) of the nonpolar isomer, exo-4-cyano-1-azaadamantane and 0.41 g (41%) of the polar isomer, endo-4-cyano-1-azaadamantane.

A solution of 0.38 g (2.34 mmol) of exo 4-cyano-1-azaadamantane in 8 ml of THF was added rapidly to a stirred solution of 4 ml of 1.0 M lithium aluminum hydride (4 mmol) in THF at room temperature. The resulting mixture was refluxed for 2 hours, cooled overnight and quenched by addition of 0.152 ml of water, 0.152 ml of 15% sodium hydroxide solution and 0.456 ml of water. The granulated aluminum salts were removed by filtration and the THF was evaporated to give 351 mg (90%) of the amine as an oil. $^1$H NMR δ2.88 (d, 2H), 4-aminomethyl CH₂. $^{13}$C NMR δ26.3 (C-7), 28.2 (C-3,5), 36.9 (C-6,10), 42.8 (C-11), 46.2 (C-4), 52.) (C-2,9), 58.3 (C-8).

EXAMPLE 11B

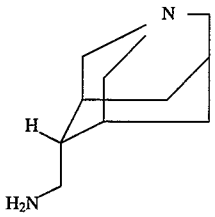

A solution of 3.8 ml of 1.0 M lithium aluminum hydride (3.80 mmol) in THF was cooled in an ice/methanol bath. Next 0.41 g (2.53 mmol) of endo 4-cyano-1-azaadamantane in 6 ml of THF was added and the mixture was allowed to warm to room temperature and then refluxed for two hours. After cooling the aluminum salts were precipitated by adding 144 μl of water in 2 ml of THF, 144 μl of 15% sodium hydroxide solution and 433 μl of water. The granulated aluminum salts were removed by filtration and the filtrate was concentrated to provide 382 mg (91%) of crude amine as a light yellow oil. $^1$H NMR δ2.83 (d, 2H) and 2.88 (d, 2H), exocyclic aminomethyl CH₂, in a 85/15 ratio that corresponds to a endo/exo mixture of 4-aminomethyl-1-azaadamantanes.

EXAMPLE 11C

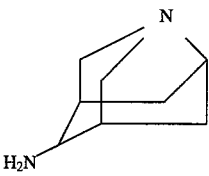

This compound was prepared by the following procedures.

Part A

Hexahydro-2,6-methano-1H-pyrrolizin-1-one (N. Speckamp, Tetrahedron, 27, 3143 (1971)), 1.45 g, 11.0 mmol, was dissolved in a 1:1 solution of pyridine/ethanol (20 mL). O-Benzyl hydroxylamine hydrochloride (1.85 g, 11.6 mmol) was added and the solution was stirred for 20 hours at room temperature. Removal of the solvents in vacuo afforded a solid which was purified by chromatography on silica gel eluting with 10% MeOH (NH₃)/CHCl₃ to give hexahydro-1-[(phenylmethoxy) imino]-2,6-methano-1H-pyrrolizine.

Anal. calc'd for C₁₅H₁₈N₂O · 0.25 H₂O: C, 72.99; H, 7.55; N, 11.35. Found: C, 73.12; H, 7.47; N, 11.44.

Part B. Syn- and Anti-
hexahydro-2,6-methano-1H-pyrrolizin-1-amine

The compound of Part A (600 mg, 2.5 mmol) was dissolved in t-amyl alcohol (40 mL). Sodium metal (740 mg, 32.0 mmol) was added to the solution and the contents heated under reflux for 7 hours. Water (20 mL) was added to the reaction mixture, which was then acidified with 1 N HCl to pH 2.0. The solution was evaporated to dryness, water (10 mL) was added and the solution was basified with 1 N NaOH to pH 14.0. The aqueous solution was extracted width chloroform, the combined extracts were dried over MgSO₄, and then evaporated to dryness to give the title compounds as a mixture of epimers (320 mg, 94%).

EXAMPLE 11D

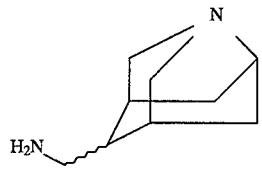

This compound was prepared by the following procedures.

Part A. Syn- and Anti-
hexahydro-2,6-methano-1H-pyrrolizin-8-carbonitriles

To a solution of hexahydro-2,6-methano-1H-pyrrolizin-1-one (1.95 g, 14.2 mmol), tosylmethylisocyanide (3.6 g, 18.5 mmol) and ethanol (1.67 mL, 28.4 mmol) in ethylene ,glycol dimethyl ether (DME) at 0° C. was added potassium t-butoxide (3.80 g, 33.8 mmol). The reaction mixture was stirred for 2 hours at room temperature followed by 2 hours at 45° C. The suspension was then filtered and the filtrate was concentrated to dryness. To the residue was added brine (40 mL) and the mixture was extracted with chloroform. The organic layer was dried over MgSO₄, filtered and concentrated to dryness. The resulting oil was purified by chromatography on silica gel, eluting with 10% MeOH (NH₃)/ chloroform to give the synnitrile (231 mg, 11%): 1H NMR (300 MHz, CDCl₃) δ1.82 (2H, dd, J=2.5, 12.5 Hz); 2.02 (2H, m); 2.49 (2H, s); 2.85 (1H, m); 2.94 (2H, d, J=12 Hz); 3.35 (2H, dd, J=2.5, 12 Hz); 3.74 (1H, t, J=7 Hz).

Continued elution gave the anti-nitrile (270 mg, 13%): 1H NMR (300 MHz, CDCl₃) δ2.01 (2H, m); 2.19 (2H, br d, J=2.5, 12.5 Hz); 2.55 (2H, br s); 3.05 (2H, br dd); 3.08 (1H, m) ; 3.11 (2H, dd, J=2.0 Hz); 3.87 (1H, s, J=7.2 Hz).

Part B. Syn- and Anti-
hexahydro-2,6-methano-1H-pyrrolizin-8-methanamines

A mixture of syn- and anti- nitriles of Part A (147 mg, 0.996 mmol) in tetrahydrofuran (THF, 3 mL) was added to a solution of 1M lithium aluminum hydride (LAH) in THF (2 mL, 1.93 mmol) at room temperature. This mixture was heated to reflux for one hour. The reaction mixture was then cooled to room temperature and 0.073 mL of water was added to quench the excess LAH. This was followed by the addition of a solution of 0.073 mL of 15% NaOH and an additional 0.220 mL of water. The resulting mixture was filtered and the solid was washed well with THF. Concentration of the filtrate gave the title compounds as a mixture of syn- and anti- isomers (147 mg, 100%).

EXAMPLE 11E

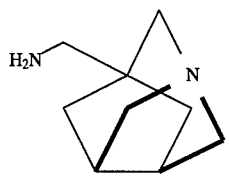

EXAMPLE A

Preparation of hexahydro-5-iodo-2,5β-methano-1H-3aα,6aα-cyclopenta [c]pyrrole

Cis-N-t-butoxycarbonylhexahydro-5-methylenecyclopenta [c]pyrrole [See co-pending application Ser. No. 07/515,391 filed Apr. 27, 1990] is treated with trifluoroacetic acid to afford an intermediate trifluoroacetate ammonium salt, which is then treated with base and 12 to afford the title compound.

EXAMPLE B

Preparation of tetrahydro-2,5β-methano-1H-3aα,6aα-cyclopenta [c]pyrrol-5(3H)-amine The iodo compound prepared in example A is treated with silver isocyanate to afford the intermediate N-formamide. This formamide is hydrolyzed to give the title compound.

EXAMPLE C

Preparation of tetrahydro-2,5β-methano-1H-3aα,6aα-cyclopenta [c]pyrrole-5(3H)-carbonitrile The iodo compound prepared in example A is treated with silver cyanide in dimethylformamide to afford the title compound.

EXAMPLE D

Preparation of tetrahydro-2,5β-methano-1H-3aα,6aα-cyclopenta [c]pyrrole-5(3H)-methanamine The nitrile compound prepared in example C is reduced with lithium aluminum hydride in etheral solvent to afford the title compound.

EXAMPLE 11F EXAMPLE 11G

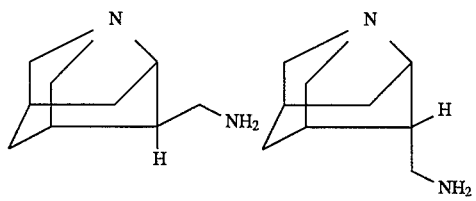

EXAMPLE A (±) Hexahydro-2,6-methano-1H-pyrrolizin-1-one

The above compound was synthesized using the method of Theo Reints Bok and Nico Speckamp [Heterocycles Vol. 12 No. 3, pages 343–347 (1979).].

EXAMPLE B

Example B-1
2S-Hexahydro-2,6-methano-1H-pyrrolizin-1-one

Example B-2
2R-Hexahydro-2,6-methano-1H-pyrrolizin-1-one

The racemic equatorial alcohol [N. Speckamp, et al. Heterocycles Vol. 12 No. 3, pages 343–347 (1979)] (30.0 g; 0.078 moles) and R-(−)-α-methoxyphenylacetic acid (13.8 g; 0.083 moles) were subjected to reflux with 100 mg of p-toluenesulfonic acid in 1.0 liter of toluene until tlc (40% EtOAc/toluene) indicated no further change. The reaction mixture was concentrated and the residue chromatographed on a Waters prep 500 using two cartridges and eluting with 5% EtOAc/CH$_2$Cl$_2$. The first compound to elute was collected in the first three 500 ml fractions. Concentration afforded 15.9 g.

HPLC Analysis

Achiral column: Zorbax-RX-C-8; Mobile Phase 10/90 to 70/30 (30 min) MeCN/TEAP Retention Time=13.46 min; 99.34% purity Chiral Column: Chiralcel OD-R; Mobile Phase 60/40 MeCN/H$_2$O Retention Time=49.40 min; 99+% purity The first component was dissolved in MeOH (500 ml) and 5.0 g of KOH in 20 ml of H$_2$O and the mixture was subjected to reflux for one hour. Tlc 40% EtOAc/toluene indicated the reaction was complete. The reaction mixture was concentrated and the residue was suspended in H$_2$O and filtered and washed with H$_2$O and suction dried to yield 7.9 g of a solid. Rotation (CHCl$_3$): $\alpha_D$+3.0°. 200 mg of this solid was crystallized from MeOH. A crystal suitable for single crystal X-ray was obtained. The absolute configuration is shown below.

This alcohol was used to prepare the enantiopure 2S-hexahydro-2,6-methano-1H-pyrrolizin-1-one (Example B-1) utilizing the synthetic route of Speckamp (Heterocycles Vol. 12, No. 3 pages 343–347 (1979)).

The second component was subjected to chromatography a second time to remove the 5% of the less polar component. The purified material was processed as described above to afford 2R-hexahydro-2,6-methano-1H-pyrrolizin-1-one (Example B-2).

EXAMPLE C (±) Hexahydro-2β,6β-methano-1H,
7aα-pyrrolizine-1α-carbonitrile (C-1) and (±)
hexahydro-2β,6β--methano-1H,
7aα-pyrrolizine-1β-carbonitrile (C-2).

3-Azanoradamantan-6-one (320 mg; 0.00233 moles) tosylmethyl isocyanide (593 mg; 0.00303 moles) and 237 μl of ethanol were dissolved in 10 ml of ethylene glycol dimethyl ether (DME). This mixture was cooled to −68° C. in an acetone/dry ice bath. Potassium tert-butoxide (623 mg; 0.0055 moles) was added to the reaction mixture, and the reaction mixture was allowed to warm to room temperature. After two hours a solid formed which was filtered and washed with DME. The filtrate was concentrated to dryness. The residue was dissolved in 2.0 ml of water and the product extracted five times with 15 ml of $Et_2O$. The combined $Et_2O$ layers were dried over $MgSO_4$ and concentrated to dryness. The resulting oil was purified by silica gel chromatography, eluting with 5% $EtOH/CHCl_3$ * 0.5% $NH_4OH$. The nitrile (C-1) (124 mg) eluted first followed by the nitrile (C-2) (105 mg).

Example C-1: $C_9H_{12}N_2$ MW=148.20 NMR ($CDCl_3$)

$^1H$ (ppm): 1.62 (1H) doublet of triplets [J=13 Hz and J=2.5 Hz]; 1.82 (1H) doublet of doublet [J=13 Hz and J=5 Hz]; 1.9 to 2.05 (2H) multiplet; 2.22 (1H) singlet; 2.5 (1H) singlet; 2.87 (1H) doublet [J=13 Hz]; 2.42 (1H) singlet; 3.06 (1H) doublet of doublets [J=11 Hz and J=3 Hz]; 3.19 (1H) doublet of doublets [J=11 Hz and J=3 Hz]; 3.43 (1H) doublet of triplets [J=11 Hz and J=1 Hz]; 3.90 (1H) doublet [J=8]. CMR -($CDCl_3$)

$^{13}C$ (ppm); 33.65; 36.37; 41.40; 43.45; 44.38; 65.41; 65.61; 67.35; 121.42.

Example C-2: $C_9H_{12}N_2$ MW = 148.20 NMR ($CDCl_3$)

$^1H$ (ppm): 1 8 to 2.0 (3H) multiplet; 2.25 (1H) singlet; 2.4 to 2.5 (2H) multiplet; 2.89 to 3.17 (5H) multiplet; 3.82 (1H) triplet [ J=13 Hz ]; CMR ($CDCl_3$)

$^{13}C$ (ppm) 30.37; 36.08; 38.46; 40.39; 40.67; 61.85; 66.25; 67.14; 123.42.

Similarly, the enantiomerically pure 3-azanoradamant-6-one isomers were reacted with tosylmethyl isocyanide to produce the enantiomerically pure nitriles.

Example C-3: Prepared from Example B-1 Hexahydro-2β,6β-methano-1H,7aα-pyrrolizine-1S,1α carbonitrile Example C-4: Prepared from Example B-2 Hexahydro-2β,6β-methano-1H,7aα-pyrrolizine-1R,1α-carbonitrile

EXAMPLE D (±)
Hexahydro-2β,6β-methano-1H,7aα-pyrrolizine-1α-methanamine

The nitrile of example C-1 (124 mg; 0.00083 moles) was added to a mixture of 1M LAH/THF (Lithium Aluminum, Hydride in Tetrahydrofuran) 1.0 ml and 1.0 ml of THF at room temperature. This mixture was heated to reflux for one hour. The reaction mixture was cooled and a solution of 100 μl water in 1.0 ml of THF was added to quench the excess LAH. This was followed by the addition of a solution of 100 μl 1 15% NaOH in 1.0 ml of THF. The resulting mixture was filtered and the solid washed with THF. The filtrate was concentrated to give 116 mg of the title compound as an oil.

$C_9H_{16}N_2$ MW=152.22 NMR ($CDCl_3$)

$^1H$ (ppm): 1.58 (1H) doublet of triplets [J=13 Hz and J=2.5 Hz ]; 1.8 to 2.0 (2H) multiplet; 2.04 (1H) triplet [J=7.5 Hz]; 2.15 (1H) singlet; 2.21 (1H) singlet; 2.55 to 2.72 (3H) multiplet; 2.85 to 3.07 (3H); 3.14 (1H) doublet of triplets [J=11 Hz and J=1 Hz]; 3.49 doublet (1H) [ J=6]. CMR ($CDCl_3$)

$^{13}C$ (ppm): 34.73; 36.34; 38.76; 43.11; 44.26; 58.11; 62.92; 64.15; 66.92.

Example D-1 (Prepared from Example C-3) Hexahydro-2β,6β-methano-1H,7aα-pyrrolizine-1S,1α-methanamine In an identical manner, the enantiomerically pure nitrile of Example C-3 was reacted to afford the title compound.

Example D-2 (Prepared from Example C-4) Hexahydro-2β,6β-methano-1H,7aα-pyrrolizine-1R,1α-methanamine In an identical manner, the enantiomerically pure nitrile of Example C-4 was reacted to afford the title compound.

EXAMPLE E (±)
Hexahydro-2β,6β-methano-1H,7aα-pyrrolizine-1β-methanamine

The nitrile of Example C-2 was reduced to the amine in the same manner as the nitrile in Example D. $C_9H_{16}N_2$ MW=152.22 NMR ($CDCl_3$)

$^1H$ (ppm): 1.4 to 1.7 (4H) multiplet; 1.9 to 2.0 (2H) multiplet; 2.05 to 2.15 (2H) multiplet; 2.45 to 2.75 (1H) multiplet; 2.8 to 3.0 (4H) multiplet; 3.61 (1H) triplet [J=11 Hz]; CMR ($CDCl_3$)

$^{13}C$ (ppm): 28.44; 33.43; 35.95; 36.95; 41.13; 52.10; 62.34; 65.57; 66.04.

EXAMPLE 11H

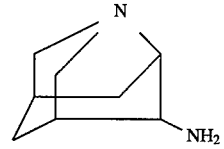

Part A. 3-Azanoradamantan-6-oxime

3-Azanoradamantan-6-one (T. R. Bok and N. Speckamp, Heterocycles, Vol. 12, no. 3, pp. 343–347 (1979) (592 mg, 0.0043 mole) and hydroxylamine hydrochloride (312 mg, 0.00034 mole) were dissolved in 10 mL of pyridine and stirred for 1 hour at room temperature. The resulting solid was filtered and washed with pyridine to afford 527 mg (80%) of the oxime.

Part B. endo- and exo-3-Azanoradamantan-6-amine

The oxime of Part A (527 mg, 0.0034 mole) was added to a mixture of 1M LAH/THF (4.0 mL) and 15 mL of THF at room temperature. This mixture was heated to reflux for 2 hours. The reaction mixture was then cooled and a solution of 300 μL of water in 3.0 mL of THF was added to quench the excess LAH. This was followed by the addition of a solution of 300 μL 15% NaOH in 3.0 mL THF. The resulting mixture was filtered and the solid washed well with THF. The filtrate was concentrated to give 167 mg (29%) of the title compound as an oil.

$^{13}C$ NMR ($CDCl_3$) 6 27.81; 32.66; 35.62; 40.75; 57.95; 63.35; 63.40; 66.07.

EXAMPLE 11J

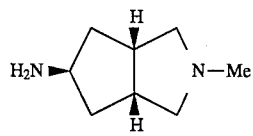

This compound was prepared by the following procedures.

Part A. 3-Aza-3-(1,1-dimethylethyloxycarbonyl)-7-(O-benzyloxyimino)bicyclo [3.3.0]octane 3-Aza-3-(1,1-dimethylethyloxycarbonyl)-7-one [D. L. Flynn et al, Bioorganic and Medicinal Chemistry Letters, Vol. 2, no. 12, pp. 1613–1618 (1992)] (23.55 g, 0.104 mole) was dissolved in a solution of 1:1 pyridine/EtOH (200 mL). To this solution was added O-benzyl hydroxylamine hydrochloride (18.35 g, 0.115 mole). After completion of the reaction, the solution was concentrated to dryness. The residue was chromatographed on silica gel eluting with 30/70 ethyl acetate/heptane to give the title compound (33.5 g, 82%).

Part B. 3-Aza-3-methyl-7-(O-benzyloxyiminobicyclo[3.3.0]octane

To the compound of Part A (5.92 g, 0.0179 mole) was added trifluoroacetic acid (30 mL). The solution was stirred at room temperature for 2 hours. The solution was concentrated to dryness. To the oil was added a solution of 20% $K_2CO_3$ and the mixture was extracted with chloroform. Concentration afforded an oil. The oil was dissolved in 35% aqueous formaldehyde (7.68 mL, 0.089 mole) in acetonitrile (60 mL). Sodium cyanoborohydride (1.23 g, 0.017 mole) was added portion-wise at 0° C. The solution was stirred for 30 minutes. The mixture was then neutralized with 1N HCl to pH 7.0, and then concentrated to dryness. To this residue was added 1N NaOH (25 mL). The mixture was extracted with chloroform, dried over $K_2CO_3$, filtered, and concentrated in vacuo to give an oil. The oil was purified by chromatography on silica gel, eluting with 4% methanol/chloroform to afford the title compound (3.74 g, 86%).

Anal. calc'd for $C_{15}H_{20}N_2O \cdot 0.1 H_2O$: C, 73.20; H, 8.27; N, 11.38. Found: C, 73.28; H, 8.21; N, 11.50

Part C. Exo-3-aza-3-methyl-7-aminobicyclo[3.3.0]-octane, trifluoroacetate salt The compound of Part B (3.74 g, 0.0153 mole) was dissolved in t-amyl alcohol (200 mL). Sodium metal (3.84 g, 0.158 mole) was added, and the mixture heated to reflux for 5 hours. The solution was cooled to 0° C., acidified to pH 2.0 with 1N HCl, and then evaporated to dryness. To this residue was added water (40 mL), 1N NaOH (50 mL), and the mixture then extracted with chloroform. The organic layer was dried over $MgSO_4$, and filtered to afford a 1:1 mixture of exo- and endo-amines (1.95 g, 91%). The amine mixture was dissolved in THF (50 mL) and then cooled to −60° C. Di-t-butylcarbonate (2.73 g, 12.5 mmole) was added portionwise. The mixture was dissolved in chloroform, washed with water, dried over $K_2CO_3$, filtered, and concentrated to give an oil. The exo- and endo- isomers were separated by chromatography on silica gel eluting with 10% methanol ($NH_3$)/chloroform to give the pure endo-(482 mg) and exo-(21%) BOC-amines. To the exo-BOC amine (157 mg, 0.653 mmole) was added trifluoroacetic acid (1 mL). The solution was stirred for 2 hours at room temperature. Concentration afforded the title compound (100%).

$^1$H NMR (300 MHz, $CD_3OD$) δ 1.49 (2H, m); 2.08 (2H, m); 2.79 (1H, m); 2.91 (3H, s); 3.08 (1H, m); 3.26 (2H, m); 3.49 (1H, m); 3.85 (2H, m).

EXAMPLE 11K

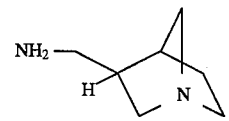

exo-3-Aminomethyl-1-azabicyclo[2.2.1]heptane exo-3-Cyano-1-azabicyclo[2.2.1]heptane (157 mg, 1.29 mmol, ca. 95:5 exo/endo) was dissolved in methanol saturated with ammonia gas and hydrogenated over Raney-Nickel (60 psi $H_2$, room temp, 3 hours). The mixture was filtered to remove catalyst and the solvent removed in vacuo. The residue was taken up into a saturated aqueous $K_2CO_3$ solution (10 mL) and extracted with chloroform (3×10 mL). The extracts were dried ($Na_2SO_4$), filtered and evaporated in vacuo to give the crude amine (104 mg, 64%). The volatile amine was used without further purification in the next step.

$^1$H NMR ($CDCL_3$) δ2.98 (dt, J=3, 11 Hz, 1 H), 2.92 (m, 1 H), 2.78–2.35 (6H), 2.02 (m, 1H), 1.88 (ddd, 1 H, J=3, 6, 12 Hz), 1.68 (br s, 2 H), 1.57–1.38 (2H). $^{13}$C NMR ($CDCl_3$) δ61.0, 58.7, 54.4, 44.1, 42.9, 38.6, 22.8.

EXAMPLE 11L

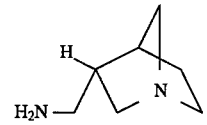

endo-3-Aminomethyl-1-azabicyclo[2.2.1]heptane endo-3-Cyano-1-azabicyclo[2.2.1]heptane (370 mg, 3.03 mmol, ca. 95:5 endo/exo) was dissolved in methanol saturated with ammonia gas and hydrogenated over Raney-Nickel (60 psi $H_2$, room temperature, 6 hours). The mixture was filtered to remove catalyst and the solvent removed in vacuo. The residue was taken up into a saturated aqueous $K_2CO_3$ solution (10 mL) and extracted with chloroform (4×10 mL). The extracts were dried ($Na_2SO_4$), filtered and evaporated in vacuo to give the crude amine (354 mg, 92%). The volatile amine was used without further purification in the next step. $^1$H NMR ($CDCl_3$) δ 2.70 (m, 1H), 2.70–2.60 (m, 2H), 2.48–2.30 (5H), 2.25 (m, 1H), 1.70–1.55 (3H), 1.41 (m, 1H), 1.12 (m, 1H). $^{13}$C NMR ($CDCl_3$) δ59.0, 56.7, 53.1, 45.8, 45.2, 39.3, 30.3.

EXAMPLE 12

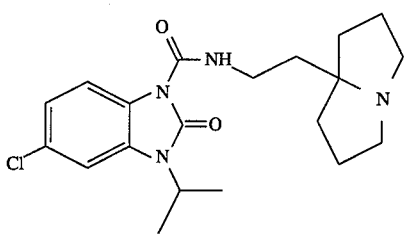

5-chloro-N-[2-(hexahydro-7aH-pyrrolizin-7a-yl)ethyl]2,3-dihydro-3-(1-methylethyl)-2-oxo-1H-benzimidazole 1-carboxamide 60% NaH/Mineral oil (80 mg; 0.002 mole) was washed with hexane and suspended in THF. 6-chloro-1,3-dihydro-1-(1-methylethyl)-2H-benzimidazol-2-one (105 mg; 0.0005 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and 7a-(2-aminoethyl)hexahydro-1H-pyrrolizine [the Journal of Heterocyclic Chemistry, 24, 271 (1987)] (77 mg; 0.0005 mole) was added with 0.5 ml of Et₃N. This mixture was stirred 1 hr., filtered and the filtrate concentrated. The residue was chromatographed first on a 2 mm Chromatron plate, and the semi-purified fraction containing the product was rechromatographed on a prep tlc plate, in both cases eluting with 20%MeOH/CHCl₃/0.25%NH₄OH. The product was washed from the silica with 5%NH₄OH/MeOH. The filtrate was concentrated and the residue was dissolved in CHCl₃ and filtered through celite and concentrated. 51 mg (26%) of product was isolated. The product was converted to the HCl salt by dissolving 11.1 µl of acetyl chloride in 5.0 ml of MeOH and adding this solution to the product, then concentrating to dryness.

$C_{20}H_{27}ClN_4O_2$ * 1.2 HCl M.W. 437.67

| Elements | Calc | Found |
|---|---|---|
| Carbon | 55.27 | 55.57 |
| Hydrogen | 6.54 | 6.42 |
| Nitrogen | 12.89 | 12.89 |
| Chlorine | 17.94 | 17.88 |

EXAMPLE 12A

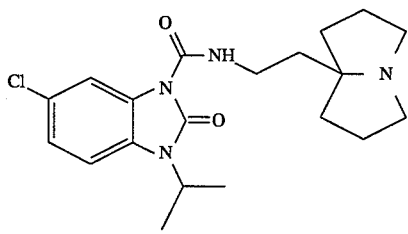

6-Chloro-N-[2-(hexahydro-7aH-pyrrolizin-7a-yl)ethyl]2,3-dihydro-3-(1-methylethyl)-2-oxo-1H-benzimidazole 1-carboxamide The procedure of Example 12 was used to synthesize the product, starting with 77 mg; 0.0005 moles of the 7a-(2-aminoethyl) hexahydro-1H-pyrrolizine [The Journal of Heterocyclic Chemistry, 24, 271 (1987)]. This yielded 2 mg (83%) of product. The product was converted to the HCl salt by dissolving 40 µl of acetyl chloride in 5.0 ml of MeOH and adding this solution to the product, then concentrating to dryness.

$C_{20}H_{27}ClN_4O_2$ ·0.9 HCl H₂O M.W. 441.74

| Elements | Calc | Found |
|---|---|---|
| Carbon | 54.38 | 54.27 |
| Hydrogen | 6.82 | 6.61 |
| Nitrogen | 12.68 | 12.55 |
| Chlorine | 15.25 | 15.26 |

EXAMPLE 12B

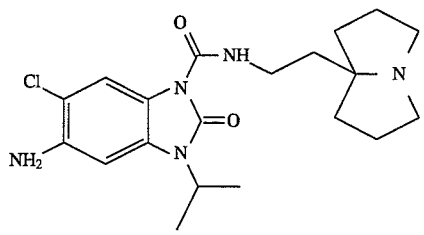

6-Chloro-5-amino-N-[2-(hexahydro-7aH-pyrrolizin-7a-yl)ethyl]-2,3-dihydro-3-(1-methylethyl)-2-oxo-1H-benzimidazole-1-carboxamide 60% NaH/Mineral oil (80 mg; 0.002 mole) was washed with hexane and suspended in THF. 1-isopropyl-5-chloro-6-nitro-2-benzimidazolinone (191 mg; 0.00075 mole) was added to the suspension. This mixture was stirred 15 minutes before adding to a mixture of 2.5 ml (0.004 mole) 20% phosgene/2.5 ml THF. The resulting mixture was filtered through celite and concentrated. The residue was redissolved in THF (5.0 ml) and 7a-(2-aminoethyl)hexahydro-1H-pyrrolizine [The Journal of Heterocyclic Chemistry, 24, 271 (1987)] (115 mg; 0.00075 mole) was added with 0.5 ml of Et₃N. This mixture was stirred 1 hour, filtered and the filtrate concentrated. The residue was chromatographed first on a prep tlc plate, eluting with 15%MeOH/CHCl₃/0.25 NH₄OH. The product was washed from the silica with THF/MeOH. The filtrate was concentrated and the residue was redissolved in CHCl₃ and filtered through celite and concentrated. 84 mg (27%) of product was isolated.

This product was hydrogenated over 5% Pt/C in ethanol until the theoretical amount of hydrogen was absorbed. The filtrate from the hydrogenation was concentrated and the residue was chromatographed on a prep tlc plate, eluting with 20% MeOH/CHCl₃/0.25 NH₄OH. The product was washed from the silica with CHCl₃/MeOH. The filtrate was concentrated and the residue was redissolved in CHCl₃ and filtered through celite and concentrated. 58 mg (77%) of product was isolated. The product was converted to the HCl salt by dissolving 26 µl of acetyl chloride in 5.0 ml of MeOH and adding this solution to the product, then concentrating to dryness.

$C_{20}H_{28}ClN_5O_2$ * 1.8 HCl · 0.75 $H_2O$ M.W. 485.07

| Elements | Calc | Found |
|---|---|---|
| Carbon | 49.52 | 49.44 |
| Hydrogen | 6.50 | 6.46 |
| Nitrogen | 14.44 | 14.20 |
| Chlorine | 20.46 | 20.13 |

EXAMPLE 13

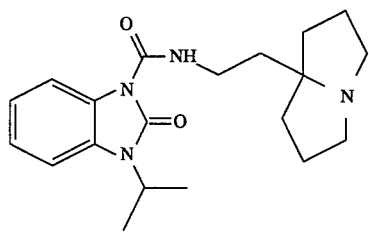

N-[2-(hexahydro-7aH-pyrrolizin-7a-yl)ethyl]-2,3-dihydro-3-(1-methylethyl) 2-oxo-1H-benzimidazole-1-carboxamide 60% NaH/Mineral oil (80 mg; 0.002 mole) was washed with hexane and suspended in THF. 1,3-dihydro-1-(1-methylethyl)-2H-benzimidazol-2-one (176 mg; 0.001 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and 7a-(2-aminoethyl)hexahydro-1 H-pyrrolizine (77 mg; 0.0005 mole) was added with 0.5 ml of Et₃N. This mixture was stirred 1 hr., filtered and the filtrate concentrated. The residue was chromatographed on a prep tlc plate, eluting with 20%MeOH/CHCl₃/0.25%NH₄OH. The product was washed from the silica with 5%NH₄OH/MeOH. The filtrate was concentrated and the residue was dissolved in CHCl₃ and filtered through celite and concentrated. 149 mg (83.7%) of product was isolated. The product was converted to the HCl salt by dissolving 35.6 μl of acetyl chloride in 5.0 ml of MeOH and adding this solution to the product, then concentrating to dryness.

$C_{20}H_{28}N_4O_2$ * 1.2 HCl * 0.25 $H_2O$ M.W. 437.67

| Elements | Calc | Found |
|---|---|---|
| Carbon | 59.21 | 58.94 |
| Hydrogen | 7.63 | 7.27 |
| Nitrogen | 13.78 | 13.78 |
| Chlorine | 10.49 | 10.25 |

EXAMPLE 13A

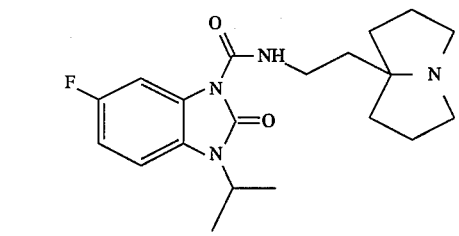

6-fluoro-N-[2-(hexahydro-7aH-pyrrolizin-7a-yl)ethyl]-2,3-dihydro-3-(1-methylethyl) 2-oxo-1H-benzimidazole-1-carboxamide 60% NaH/Mineral oil (80 mg; 0.002) was washed with hexane and suspended in THF. 6-fluoro-1,3-dihydro-1-(1-methylethyl)-2H-benzimidazol-2-one (145 mg; 0.00075 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and 7a-(2-aminoethyl) hexahydro-1H-pyrrolizine [the Journal of Heterocyclic Chemistry, 24, 271 (1987)] (77 mg; 0.0005 mole) was added with 0.5 ml of Et₃N. This mixture was stirred 1 hr., filtered and the filtrate concentrated. The residue was chromatographed first on a 2 mm Chromatron plate, and the semi-purified fraction containing the product was rechromatographed on a prep tlc plate, in both cases eluting with 10%MeOH/CHCl₃/0.25%NH₄OH. The product was washed from the silica with 5%NH₄OH/MeOH. The filtrate was concentrated and the residue was dissolved in CHCl₃ and filtered through celite and concentrated. 105 mg (56%) of product was isolated. The product was converted to the HCl salt by dissolving 11.1 μl of acetyl chloride in 5.0 ml of MeOH and adding this solution to the product, and then concentrating to dryness.

$C_{20}H_{27}FN_4O_2$ * 1.1 HCl * $H_2O$ M.W. 432.58.

| Elements | Calc | Found |
|---|---|---|
| Carbon | 55.53 | 55.62 |
| Hydrogen | 7.01 | 7.01 |
| Nitrogen | 12.95 | 12.91 |
| Chlorine | 9.02 | 9.35 |

EXAMPLE 13B

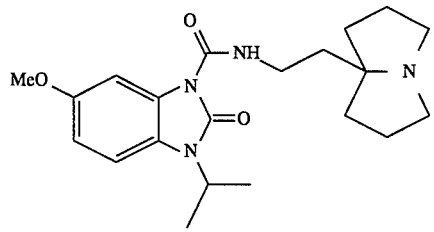

N-[2-(hexahydro-7aH-pyrrolizin-7a-yl)ethyl]-2,3-dihydro-6-methoxy-3 (1-methylethyl)-2-oxo-1H-benzimidazole-1-carboxamide 60% NaH/Mineral oil (8 mg; 0.002) was washed with hexane and suspended in THF. 1,3-dihydro-6-methoxy-1-

(1-methylethyl)-2H-benzimidazol-2-one (154 mg; 0.00075 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and 7a-(2-aminoethyl)hexahydro-1H-pyrrolizine [the Journal of Heterocyclic Chemistry, 24, 271 (1987)] (77 mg; 0.0005 mole) was added with 0.5 ml of $Et_3N$. This mixture was stirred 1 hr., filtered and the filtrate concentrated. The residue was chromatographed first on a 2 mm Chromatron plate, and the semi-purified fraction containing the product was rechromatographed on a prep tlc plate, in both cases eluting with 10% $MeOH/CHCl_3/0.25\%NH_4OH$. The product was washed from the silica with 5% $NH_4OH/MeOH$. The filtrate was concentrated and the residue was dissolved in $CHCl_3$ and filtered through celite and concentrated. 118 mg (61%) of product was isolated. The product was converted to the HCl salt by dissolving 11.1 µl of acetyl chloride in 5.0 ml of MeOH and adding this solution to the product, then concentrating to dryness.

$C_{21}H_{30}N_4O_3$ * HCl * 1.25 $H_2O$ M.W. 445.48.

| Elements | Calc | Found |
| --- | --- | --- |
| Carbon | 56.62 | 56.64 |
| Hydrogen | 7.58 | 7.48 |
| Nitrogen | 12.58 | 12.52 |
| Chlorine | 7.96 | 7.74 |

EXAMPLE 13C

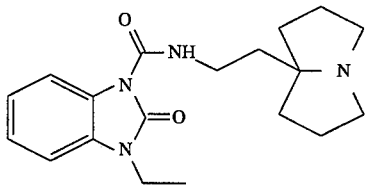

3-ethyl-N-[(hexahydro-7aH-pyrrolizin-7a-yl)ethyl]-2,3-dihydro-2-oxo-1H benzimidazole-1-carboxamide 60% NaH/Mineral oil (80 mg; 0.002) was washed with hexane and suspended in THF. 1-ethyl-1,3-dihydro-2H-benzimidazol-2-one (121 mg; 0.00075 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and 7a-(2-aminoethyl) hexahydro-1H-pyrrolizine [the Journal of Heterocyclic Chemistry, 24, 271 (1987)] (77 mg; 0.0005 mole) was added with 0.5 ml of $Et_3N$. This mixture was stirred 1 hr., filtered and the filtrate concentrated. The residue was chromatographed on a prep tlc plate, eluting with 10% $MeOH/CHCl_3/0.25\ NH_4OH$. The product was washed from the silica with 5% $NH_4OH/$MeOH. The filtrate was concentrated and the residue was dissolved in $CHCl_3$ and filtered through celite and concentrated. 147 mg (86%) of product was isolated. The product was converted to the HCl salt by dissolving 16 µl of acetyl chloride in 5.0 ml of MeOH and adding this solution to the product, then concentrating to dryness.

$C_{19}H_{26}N_4O_2$ * 1 HCl * 1.25 $H_2O$ M.W. 380.53.

| Elements | Calc | Found |
| --- | --- | --- |
| Carbon | 59.97 | 59.69 |
| Hydrogen | 6.65 | 6.52 |
| Nitrogen | 14.72 | 14.67 |
| Chlorine | 10.25 | 10.40 |

EXAMPLE 14

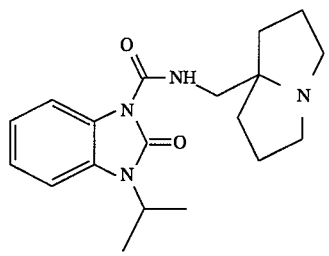

N-[(hexahydro-7aH-pyrrolizin-7a-yl)methyl]-2,3-dihydro-3-(1-methylethyl) 2-oxo-1H-benzimidazole-1-carboxamide 60% NaH/Mineral oil (80 mg; 0.002 mole) was washed with hexane and suspended in THF. 1,3-dihydro-1-(1-methylethyl)-2H-benzimidazol-2-one (176 mg; 0.001 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and 7a-aminomethylhexahydro-1H-pyrrolizine [the Journal of Heterocyclic Chemistry, 24, 47(1987)] (70 mg; 0.0005 mole) was added with 0.5 ml of $Et_3N$. This mixture was stirred 1 hr., filtered and the filtrate concentrated. The residue was chromatographed on a prep tlc plate, eluting with 10%$MeOH/CHCl_3/0.25\%NH_4OH$. The product was washed from the silica with 5%$NH_4OH/$MeOH. The filtrate was concentrated and the residue was dissolved in $CHCl_3$ and filtered through celite and concentrated. 149 mg (83.7%) of product was isolated. The product was converted to the HCl salt by dissolving 35.6 µl of acetyl chloride in 5.0 ml of MeOH and adding this solution to the product, then concentrating to dryness.

$C_{19}H_{26}N_4O_2$ * 1.15 HCl * 0.5 $H_2O$ M. W. 394.39

| Elements | Calc | Found |
| --- | --- | --- |
| Carbon | 57.86 | 57.88 |
| Hydrogen | 7.45 | 7.07 |

| Elements | Calc | Found |
|---|---|---|
| Nitrogen | 14.21 | 13.83 |
| Chlorine | 10.13 | 10.13 |

EXAMPLE 14A

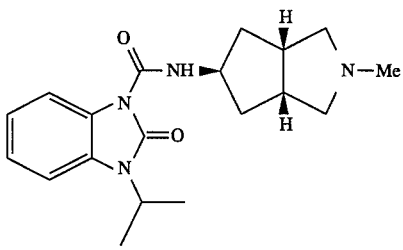

N-(exo-3-aza-3-methylbicyclo[3,.3.0]octan-7-yl)-3-
(1-methylethyl-2,3-dihydro
2-oxo-1H-benzimidazole-1-carboxamide A 60% NaH/mineral oil dispersion (100 mg, 2.61 mmol) was washed with hexane and suspended in THF (1.0 mL). 1-isopropyl-1,3-dihydro-2H-benzimidazol-2-one (115 mg, 0.653 mmol) was added to the suspension. This mixture was stirred for 15 minutes before adding it to a mixture of 2.38 mL (5.22 mmol) of 20% phosgene (toluene)/2.6 mL THF. The resulting mixture was stirred for 2.5 hours, filtered through celite, and concentrated. The residue was redissolved in THF (2.0 mL) and the amine of Example 11J (166 mg, 0.653 mmol) was added with triethylamine (0.137 mL, 0.98 mmol). This mixture was stirred for 18 hours and then concentrated to dryness. The residue was dissolved in chloroform, washed with saturated aqueous $K_2CO_3$, water, and then dried over $K_2CO_3$. Filtration and concentration afforded an oil. Purification by chromatography on silica gel eluting with 5% methanol($NH_3$)/chloroform gave 86 mg (27%) of the title compound.

Mp=195.4°–195.8° C. Anal. calc'd for $C_{19}H_{26}N_4O_2 \cdot 0.25 H_2O$: C, 65.78; H, 7.78; N, 16.15. Found: C, 65.71; H, 7.42; N, 16.04.

EXAMPLE 15

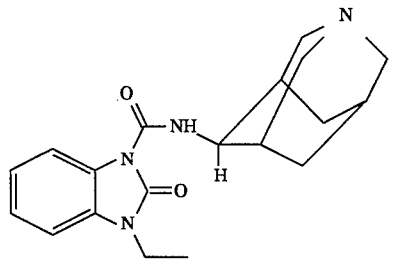

N-(1-azatricyclo[3.3.1.1$^{3,7}$]decan-4-yl)-3-ethyl-2,3-
dihydro-2-oxo 1H-benzimidazole-1-carboxamide 60% NaH/Mineral oil (80 mg; 0.002 mole) was washed with hexane and suspended in THF. 1-ethyl-1,3-dihydro-2H-benzimidazol-2-one (121 mg; 0.00075 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and the compound prepared in Example 9 (104 mg; 0.00075 mole) was added with 0.5 ml of $Et_3N$. This mixture was stirred 1 hr., filtered and the filtrate concentrated. The residue was chromatographed on a prep tlc plate, eluting with 10%MeOH/$CHCl_3$/0.25 $NH_4OH$. The product was washed from the silica with 5%$NH_4OH$/MeOH. The filtrate was concentrated and the residue was dissolved in $CHCl_3$ and filtered through celite and concentrated. 184 mg (74%) of product was isolated. The product was converted to the HCl salt by dissolving 16 µl of acetyl chloride in 5.0 ml of MeOH and adding this solution to the product, then concentrating to dryness.

$C_{19}H_{24}N_4O_2$ * 1.1 HCl M.W. 380.53

| Elements | Calc | Found |
|---|---|---|
| Carbon | 59.97 | 59.69 |
| Hydrogen | 6.65 | 6.52 |
| Nitrogen | 14.72 | 14.67 |
| Chlorine | 10.25 | 10.40 |

EXAMPLE 16

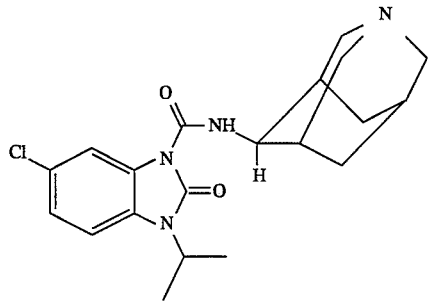

N-(1-azatricyclo[3.3.1.1$^{3,7}$]decan-4-yl)-6-chloro-2,3
-dihydro-3-(1-methylethyl)
2-oxo-1H-benzimidazole-1-carboxamide 60% NaH/Mineral oil (80 mg; 0.002 mole) was washed with hexane and suspended in THF. 5-chloro-1,3-dihydro-1-(1-methylethyl)-2H-benzimidazol-2-one (157 mg; 0.00075 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and the compound prepared in Example 9 (104 mg; 0.00075 mole) was added with 0.5 ml of $Et_3N$. This mixture was stirred 1 hr., filtered and the filtrate concentrated. The residue was chromatographed on a prep tlc plate, eluting with 10%MeOH/$CHCl_3$/0.25%$NH_4OH$. The product was washed from the silica with 5%$NH_4OH$/MeOH. The filtrate was concentrated and the residue was dissolved in $CHCl_3$ and filtered through celite and concentrated. 184 mg (74%) of product was isolated. The product was converted to the HCl salt by dissolving 26 µl of acetyl chloride in 5.0 ml of MeOH and adding this solution to the product, then concentrating to dryness.

$C_{20}N_{25}ClN_4O_2$ * 1.05 HCl * 0.5 $H_2O$ M.W. 436.19

| Elements | Calc | Found |
|---|---|---|
| Carbon | 55.07 | 55.27 |
| Hydrogen | 6.25 | 5.98 |
| Nitrogen | 12.84 | 12.85 |
| Chlorine | 16.66 | 16.87 |

EXAMPLE 17

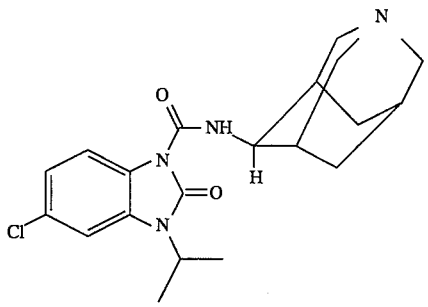

N-(1-azatricyclo[3.3.1.1$^{3,7}$]decan-4-yl)-5-chloro-2,3-dihydro-3-(1-methylethyl)
2-oxo-1H-benzimidazole-1-carboxamide 60% NaH/Mineral oil (80 mg; 0.002 mole) was washed with hexane and suspended in THF. 6-chloro-1,3-dihydro-1-(1-methylethyl)-2H-benzimidazol-2-one (157 mg; 0.00075 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and the compound prepared in Example 9 (104 mg; 0.00075 mole) was added with 0.5 ml of Et$_3$N. This mixture was stirred 1 hr., filtered and the filtrate concentrated. The residue was chromatographed on a prep tlc plate, eluting with 10%MeOH/CHCl$_3$/0.25%NH$_4$OH. The product was washed from the silica with 5%NH$_4$OH/MeOH. The filtrate was concentrated and the residue was dissolved in CHCl$_3$ and filtered through celite and concentrated. 150 mg (53%) of product was isolated. The product was converted to the HCl salt by dissolving 30 μl of acetyl chloride in 5.0 ml of MeOH and adding this solution to the product, then concentrating to dryness.

$C_{20}H_{25}ClN_4O_2$ * HCl * $H_2O$ M.W. 44 3.38

| Elements | Calc | Found |
|---|---|---|
| Carbon | 54.18 | 54.38 |
| Hydrogen | 6.37 | 6.06 |
| Nitrogen | 12.64 | 12.66 |
| Chlorine | 15.99 | 16.27 |

EXAMPLE 18

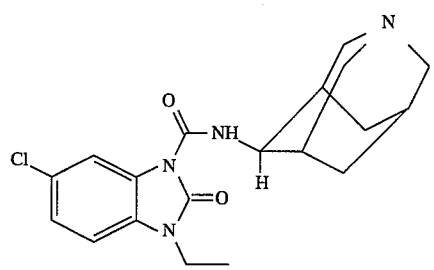

N-(1-azatricyclo[3.3.1.1$^{3,7}$]decan-4-yl)-6-chloro-3-ethyl-2,3-dihydro
2-oxo-1H-benzimidazole-1-carboxamide 60% NaH/Mineral oil (80 mg; 0.002 mole) was washed with hexane and suspended in THF. 5-chloro-1-ethyl-1,3-dihydro-2H-benzimidazol-2-one (147 mg; 0.00075 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and the compound prepared in Example 9 (104 mg; 0.00075 mole) was added with 0,.5 ml of Et$_3$N. This mixture was stirred 1 hr., filtered and the filtrate concentrated. The residue was chromatographed on a prep tlc plate, eluting with 10%MeOH/CHCl$_3$/0.25%NH$_4$OH. The product was washed from the silica with 5%NH$_4$OH/MeOH. The filtrate was concentrated and the residue was dissolved in CHCl$_3$ and filtered through celite and concentrated. 200 mg (73%) of product was isolated. The product was converted to the HCl salt by dissolving 42 μl of acetyl chloride in 5.0 ml of MeOH and adding this solution to the product, then concentrating to dryness.

$C_{19}H_{23}ClN_4O_2$ * HCl * 0.75 $H_2O$ M.W. 422.05

| Elements | Calc | Found |
|---|---|---|
| Carbon | 54.07 | 54.26 |
| Hydrogen | 5.83 | 5.83 |
| Nitrogen | 13.27 | 13.24 |
| Chlorine | 15.12 | 15.15 |

EXAMPLE 19

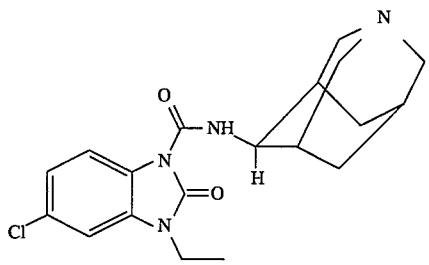

N-(1-azatricyclo[3.3.1.1$^{3,7}$]decan-4-yl)-5-chloro-3-ethyl-2,3-dihydro
2-oxo-1H-benzimidazole-1-carboxamide 60% NaH/Mineral oil (80 mg; 0.002 mole) was washed with hexane and suspended in THF. 6-chloro-1-ethyl-1,3-dihydro-2H-benzimidazol-2-one (147 mg; 0.00075 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and the compound prepared in Example 9 (104 mg; 0.00075 mole) was added with 0.5 ml of Et₃N. This mixture was stirred 1 hr., filtered and the filtrate concentrated. The residue was chromatographed on a prep tlc plate, eluting with 10%MeOH/CHCl₃/0.25%NH₄OH. The product was washed from the silica with 5%NH₄OH/MeOH. The filtrate was concentrated and the residue was dissolved in CHCl₃ and filtered through celite and concentrated. 181 mg (66%) of product was isolated. The product was converted to the HCl salt by dissolving 38 μl of acetyl .chloride in 5.0 ml of MeOH and adding this solution to the product, then concentrating to dryness.

$C_{19}H_{23}ClN_4O_2$ * 0.9 HCl * $H_2O$ M.W. 425.70

| Elements | Calc | Found |
|---|---|---|
| Carbon | 53.61 | 53.79 |
| Hydrogen | 5.75 | 5.75 |
| Nitrogen | 13.16 | 13.11 |
| Chlorine | 15.82 | 15.54 |

EXAMPLE 19A

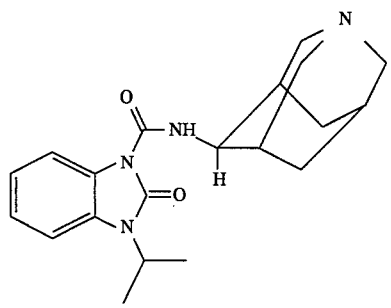

N-(1-azatricyclo[3.3.1.1$^{3,7}$]decan-4-yl)-2,3-dihydro-3-(1-methylethyl)
2-oxo-1H-benzimidazole-1-carboxamide 60% NaH/Mineral oil (80 mg; 0.002) was washed with hexane and suspended in THF. 1,3-dihydro-1-(1-methylethyl)-2H-benzimidazol-2-one (132 mg; 0.00075 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and the compound prepared in example 9 (104 mg; 0.00075 mole) was added with 0.5 ml of Et₃N. This mixture was stirred 1 hr., filtered and the filtrate concentrated. The residue was chromatographed on a prep tlc plate, eluting with 10% MeOH/CHCl₃/0.25 NH₄OH. The product was washed from the silica with 5% NH₄OH/MeOH. The filtrate was concentrated and the residue was dissolved in CHCl₃ and filtered through celite and concentrated. 118 mg (46%) of product was isolated. The product was converted to the HCl salt by dissolving 16 μl of acetyl chloride in 5.0 ml of MeOH and adding this solution to the product, then concentrating to dryness.

$C_{20}H_{26}N_4O_2$ * 1.1 HCl * 1.25 $H_2O$ M.W. 417.08.

| Elements | Calc | Found |
|---|---|---|
| Carbon | 57.60 | 57.92 |
| Hydrogen | 7.15 | 6.88 |
| Nitrogen | 13.43 | 13.39 |
| Chlorine | 9.35 | 9.26 |

EXAMPLE 19B

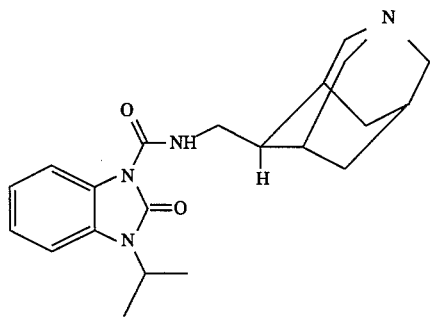

N-(1-azatricyclo[3.3.1.1$^{3,7}$]decan-4-ylmethyl)-2,3-dihydro-3-(1-methylethyl)
2-oxo-1H-benzimidazole-1-carboxamide The title compound was prepared in 40% yield according to the procedure of Example 19A, except 194 mg of 1,3-dihydro-1-(1-methylethyl)-2H-benzimidazol-2-one and 166 mg of the amine of Example 11A were used to afford 146 mg.

Anal. calc'd for $C_{21}H_{28}N_4O_2$ ·0.5 CHCl₃: C, 60.31; H, 6.71; N, 13.09. Found: C, 60.29; H, 6.62; N, 12.53.

EXAMPLE 20

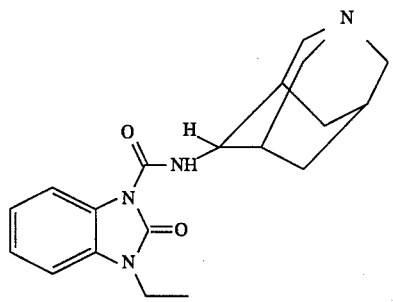

N-(1-azatricyclo[3.3.1.1$^{3,7}$]decan-4-yl)-3-ethyl-2,3-dihydro-2-oxo-1H-benzimidazole 1-carboxamide 60% NaH/Mineral oil (80 mg; 0.002 mole) was washed with hexane and suspended in THF. 1-ethyl-1,3-dihydro-2H-benzimidazol-2-one (121 mg; 0.00075 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and the compound prepared in Example 11 (104 mg; 0.00075 mole) was added with 0.5 ml of Et₃N. This mixture was stirred 1 hr., filtered and the filtrate concentrated. The residue was chromatographed on a prep tlc plate, eluting with 10%MeOH/CHCl₃/

0.25%NH₄OH. The product was washed from the silica with 5%NH₄OH/MeOH. The filtrate was concentrated and the residue was dissolved in CHCl₃ and filtered through celite and concentrated. 160 mg (64.5%) of product was isolated. The product was converted to the HCl salt by dissolving 36 μl of acetyl chloride in 5.0 ml of MeOH and adding this solution to the product, then concentrating to dryness.

$C_{19}N_{24}N_4O_2$ * 1.1 HCl * 1.25 H₂O M.W. 403.05

| Elements | Calc | Found |
|---|---|---|
| Carbon | 56.62 | 56.40 |
| Hydrogen | 6.90 | 6.71 |
| Nitrogen | 13.90 | 13.70 |
| Chlorine | 9.68 | 9.34 |

EXAMPLE 21

N-(1-azatricyclo[3.3.1.1³,⁷]decan-4-yl)-6-chloro-3-ethyl-2,3-dihydro
2-oxo-1H-benzimidazole-1-carboxamide 60% NaH/Mineral oil (80 mg; 0.002 mole) was washed with hexane and suspended in THF. 5-chloro-1,3-dihydro-1-ethyl-2H-benzimidazol-2-one (147 mg; 0.00075 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and the compound prepared in Example 11 (104 mg; 0.00075 mole) was added with 0.5 ml of Et₃N. This mixture was stirred 1 hr., filtered and the filtrate concentrated. The residue was chromatographed on a prep tlc plate, eluting with 10%MeOH/CHCl₃/ 0.25%NH₄OH. The product was washed from the silica with 5%NH₄OH/MeOH. The filtrate was concentrated and the residue was dissolved in CHCl₃ and filtered through celite and concentrated. 149 mg (54%) of product was isolated. The product was converted to the HCl salt by dissolving 31 μl of acetyl chloride in 5.0 ml of MeOH and adding this solution to the product, then concentrating to dryness.

$C_{19}H_{23}ClN_4O_2$ * HCl * H₂O * 0.75 MeOH M.W. 453.38

| Elements | Calc | Found |
|---|---|---|
| Carbon | 52.32 | 52.69 |
| Hydrogen | 6.45 | 6.18 |
| Nitrogen | 12.36 | 12.36 |
| Chlorine | 15.64 | 15.42 |

EXAMPLE 22

N-(1-azatricyclo[3.3.1.1³,⁷]decan-4-yl)-5-chloro-3-ethyl-2,3-dihydro
2-oxo-1H-benzimidazole-1-carboxamide 60% NaH/Mineral oil (80 mg; 0.002 mole) was washed with hexane and suspended in THF. 6-chloro-1-ethyl-1,3-dihydro-2H-benzimidazol-2-one (147 mg; 0.00075 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and the compound prepared in Example 11 (104 mg; 0.00075 mole) was added with 0.5 ml of Et₃N. This mixture was stirred 1 hr., filtered and the filtrate concentrated. The residue was chromatographed on a prep tlc plate, eluting with 10%MeOH/CHCl₃/ 0.25%NH₄OH. The product was washed from the silica with 5%NH₄OH/MeOH. The filtrate was concentrated and the residue was dissolved in CHCl₃ and filtered through celite and concentrated. 186 mg (68%) of product was isolated. The product was converted to the HCl salt by dissolving 39 μl of acetyl chloride in 5.0 ml of MeOH and adding this solution to the product, then concentrating to dryness.

$C_{19}H_{23}ClN_4O_2$ * HCl * H₂O M.W. 429.35

| Elements | Calc | Found |
|---|---|---|
| Carbon | 53.15 | 53.18 |
| Hydrogen | 6.10 | 5.79 |
| Nitrogen | 13.05 | 12.93 |
| Chlorine | 16.51 | 16.16 |

EXAMPLE 22A

N-(1-azatricyclo[3.3.1.1³,⁷]decan-4-yl)-2,3-dihydro-3-(1-methylethyl)
2-oxo-1H-benzimidazole-1-carboxamide 60% NaH/Mineral oil (80 mg; 0.002) was washed with hexane and suspended in THF. 1,3-dihydro-1-(1-methylethyl)-2H-benzimidazol-2-one (132 mg; 0.00075 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and the compound prepared in Example 11 (104 mg; 0.00075 mole) was added with 0.5 ml of Et$_3$N. This mixture was stirred 1 hr., filtered and the filtrate concentrated. The residue was chromatographed on a prep tlc plate, eluting with 10% MeOH/CHCl$_3$/0.25 NH$_4$OH. The product was washed from the silica with 5% NH$_4$OH/MeOH. The filtrate was concentrated and the residue was dissolved in CHCl$_3$ and filtered through celite and concentrated. 194 mg (75%) of product was isolated. The product was converted to the HCl salt by dissolving 16 µl of acetyl chloride in 5.0 ml of MeOH and adding this solution to the product and then concentrating to dryness.

$C_{20}H_{26}N_4O_2$ * 1.5 HCl * 1.75 H$_2$O M.W. 440.67.

| Elements | Calc | Found |
|---|---|---|
| Carbon | 54.51 | 54.41 |
| Hydrogen | 7.09 | 6.98 |
| Nitrogen | 12.71 | 12.47 |
| Chlorine | 12.07 | 11.76 |

EXAMPLE 22B

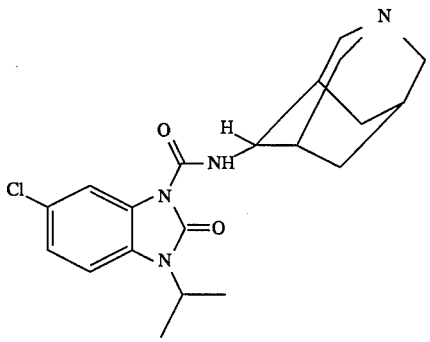

N-(1-azatricyclo[3.3.1.1$^{3,7}$]decan-4-yl)-6-chloro-2,3-dihydro-3-(1-methylethyl)
2-oxo-1H-benzimidazole-1-carboxamide 60% NaH/Mineral oil (80 mg; 0.002) was washed with hexane and suspended in THF. 5-chloro-1,3-dihydro-1-(1-methylethyl)-2H-benzimidazol-2-one (157 mg; 0.00075 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and the compound prepared in Example 11 (104 mg; 0.00075 mole) was added with 0.5 ml of Et$_3$N. This mixture was stirred 1 hr., filtered and the filtrate concentrated. The residue was chromatographed on a prep tlc plate, eluting with 10% MeOH/CHCl$_3$/ 0.25 NH$_4$OH. The product was washed from the silica with 5% NH$_4$OH/MeOH. The filtrate was concentrated and the residue was dissolved in CHCl$_3$ and filtered through celite and concentrated. 214 mg (76%) of product was isolated. The product was converted to the HCl salt by dissolving 26 µl of acetyl chloride in 5.0 ml of MeOH and adding this solution to the product and then concentrating to dryness.

$C_{20}H_{25}ClN_4O_2$ * 1.2 HCl * 2 H$_2$O M.W. 468.68.

| Elements | Calc | Found |
|---|---|---|
| Carbon | 51.25 | 51.19 |
| Hydrogen | 6.49 | 6.13 |
| Nitrogen | 11.95 | 11.85 |
| Chlorine | 16.64 | 16.61 |

EXAMPLE 22C

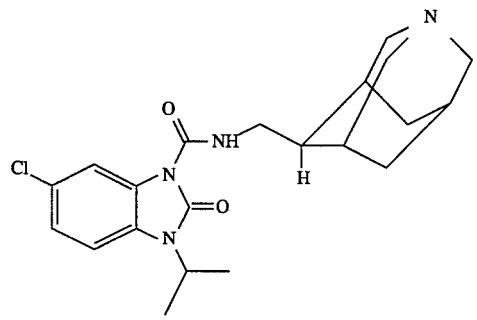

N-(1-azatricyclo[3.3.1.1$^{3,7}$]decan-4-ylmethyl)-6-chloro-2,3-dihydro-3-(1-methylethyl)
2-oxo-1H-benzimidazole-1-carboxamide The title compound was prepared according to the procedure of Example 22B, except 232 mg of 5-chloro-1,3-dihydro-1-(1-methylethyl)-2H-benzimidazol 2-one and 166 mg of the amine of Example 11A were used to afford 111 mg.

Anal. calc'd $C_{21}H_{27}N_4O_2Cl$ ·0.1 CHCl$_3$: C,61.09; H, 6.58; N, 13.51. Found: C, 61.36; H, 6.84; N, 13.56.

EXAMPLE 23

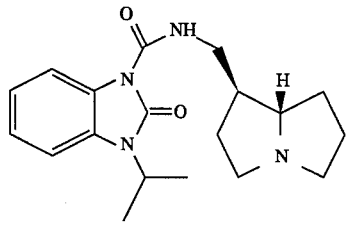

cis-N-[(hexahydro-1H-pyrrolizin-1-yl)methyl]-2,3-dihydro-3-(1-methylethyl)
2-oxo-1H-benzimidazole-1-carboxamide 60% NaH/Mineral oil (80 mg; 0.002 mole) was washed with hexane and suspended in THF. 1,3-dihydro-1-(1-methylethyl)-2H-benzimidazol-2-one (176 mg; 0.001 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and the compound prepared in Example 10 (140 mg; 0.001 mole) was added with 0.5 ml of Et$_3$N. This mixture was stirred 1 hr., filtered and the filtrate concentrated. The residue was chromatographed on a prep tlc plate, eluting with 30%MeOH/CHCl$_3$/ 0.25%NH$_4$OH. The product was washed from the silica with 5%NH$_4$OH/MeOH. The filtrate was concentrated and the residue was dissolved in CHCl₃ and filtered through celite and concentrated. 157 mg (50%) of product was isolated. The product was converted to the HCl salt by dissolving 36 µl of acetyl chloride in 5.0 ml of MeOH and adding this solution to the product, then concentrating to dryness.

$C_{19}N_{26}N_4O_2$ * HCl * $H_2O$ M. W. 396.92

| Elements | Calc | Found |
|---|---|---|
| Carbon | 57.50 | 57.44 |
| Hydrogen | 7.32 | 7.42 |
| Nitrogen | 14.12 | 13.87 |
| Chlorine | 8.93 | 8.93 |

EXAMPLE 24

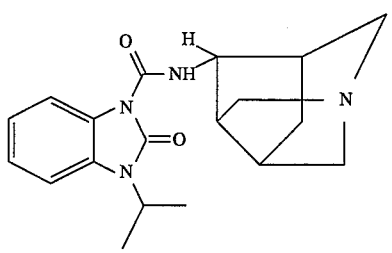

N-(hexahydro-1H-2,5β-methano-3aα,6aα-cyclopenta[c]pyrrol-4α-yl)-2,3-dihydro-3-(1-methylethyl)-2-oxo 1H-benzimidazole-1-carboxamide 60% NaH/Mineral oil (80 mg; 0.002 mole) was washed with hexane and suspended in THF. 1,3-dihydro-1-(1-methylethyl)-2H-benzimidazol-2-one (132 mg; 0.00075 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and N-(hexahydro-1H-2,5β-methano-3aα, 6aα-cyclopenta[c]pyrrol-4α-yl) amine (80 mg; 0.000578 mole) [prepared according to method of Becker et al., EP 454,121] was added with 0.5 ml of Et₃N. This mixture was stirred 1 hr., filtered and the filtrate concentrated. The residue was chromatographed on a prep tlc plate, eluting with 10%MeOH/CHCl₃/0.25 NH₄OH. The product was washed from the silica with 5%NH₄OH/MeOH. The filtrate was concentrated and the residue was dissolved in CHCl₃ and filtered through celite and concentrated. 115 mg (59%) of product was isolated. The product was converted to the HCl salt by dissolving 16 µl of acetyl chloride in 5.0 ml of MeOH and adding this solution to the product, then concentrating to dryness.

$C_{19}H_{24}N_4O_2$ * 1 HCl * 1 $H_2O$ M.W. 39.4.90

| Elements | Calc | Found |
|---|---|---|
| Carbon | 57.79 | 57.89 |
| Hydrogen | 6.89 | 6.62 |
| Nitrogen | 14.19 | 14.07 |
| Chlorine | 8.98 | 9.06 |

EXAMPLE 25

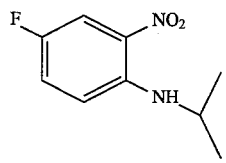

4-fluoro-N-isopropyl-2-nitroaniline 4-fluoro-2-nitroaniline (15.6 g; 0.1 mole), 2,2-dimethoxypropane (24.6 ml; 0.2 mole) and trifluoroacetic acid [TFA] (23.1 ml; 0.005 moles) were dissolved in toluene (500 ml) and stirred for 1 hr. BH₃ * pyridine (10.0 ml; 0.1 moles) was added in 1.0 ml increments. The reaction was exothermic, and the reaction progress was monitored by tlc 40% EtOAc/Hexane. Additional TFA, BH₃ * pyridine and 2,2-dimethoxypropane were added until the tlc indicated that the 4-fluoro-2-nitroaniline was consumed. The reaction mixture was placed on a bed of silica and eluted with 10% methyl-t-butylether/hexane. The product was the first major component to elute, which produced 11.2 g (58%) of a yellow oil.

$C_9H_{10}FN_2O_2$ M.W. 198.19

| Elements | Calc | Found |
|---|---|---|
| Carbon | 54.54 | 55.09 |
| Hydrogen | 5.59 | 5.63 |
| Nitrogen | 14.13 | 14.00 |

EXAMPLE 26

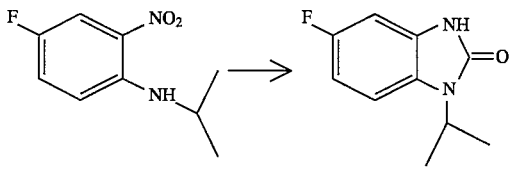

4-fluoro-N-isopropyl-2-nitroaniline→5-fluoro-1,3-dihydro-2H-benzimidazol-2-one 4-fluoro-N-isopropyl-2-nitroaniline (11.1 g; 0.0564 mole) was dissolved in MeOH (330 ml) and hydrogenated at room temperature, at 5.0 psi over Ra-Ni for 1.5 hr. at which time the theoretical hydrogen uptake had been achieved. The reaction mixture was filtered and the filtrate was concentrated. The residue was dissolved in CH₂Cl₂ (200 ml) and triphosgene (5.6 g; 0.0566 mole) dissolved in 25 ml CH₂Cl₂ was added. The reaction was exothermic. The reaction mixture was stirred for 1 hr. and then concentrated. The solid was triturated with water and filtered, washed with Et₂O and suction dried. 5.2 g (47.5%) of a purple-white solid.

$C_{10}H_{11}FN_2O$ * 0.1 $H_2O$ M.W. 197.8.

| Elements | Calc | Found |
|---|---|---|
| Carbon | 61.28 | 61.06 |
| Hydrogen | 5.76 | 5.52 |
| Nitrogen | 14.29 | 14.22 |

EXAMPLE 27

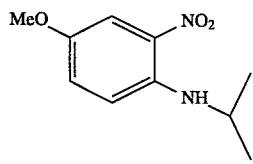

N-isopropyl-4-methoxy-2-nitroaniline 4-methoxy-2-nitroaniline (16.8 g; 0.1 mole), 2,2-dimethoxypropane (24.6 ml; 0.2 mole) and trifluoroacetic acid [TFA] (23.1 ml; 0.005 moles) were dissolved in toluene (500 ml) and stirred for 1 hr. $BH_3$ * pyridine (10.0 ml; 0.1 moles) was added in 1.0 ml increments. The reaction was exothermic, and the reaction progress was monitored by tlc 40% EtOAc/Hexane. .Additional TFA, $BH_3$ * pyridine and 2,2-dimethoxypropane were added until the tlc indicated that the 4-fluoro-2-nitroaniline was consumed. The reaction mixture was placed on a bed of silica and eluted with 10% methyl-t-butylether/hexane. The product was the first major component to elute, which produced 13.2 g (62%) of a yellow solid.

$C_{10}H_{14}N_2O_3$ M.W. 2 10.2 2.

| Elements | Calc | Found |
|---|---|---|
| Carbon | 57.13 | 57.15 |
| Hydrogen | 6.71 | 6.78 |
| Nitrogen | 13.32 | 13.33 |

EXAMPLE 28

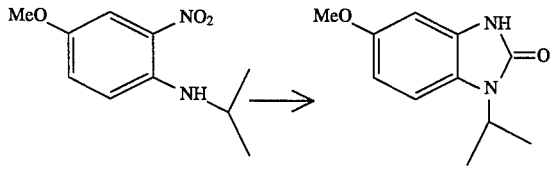

N-isopropyl-4-methoxy-2-nitroaniline→1,3-dihydro-5-methoxy-1-(1-methylethyl)
2H-benzimidazol-2-one N-isopropyl-4-methoxy-2-nitroaniline (13.1 g; 0.0627 mole) was dissolved in MeOH (330 ml) and hydrogenated at room temperature, at 5.0 psi over Ra-Ni for 1.5 hr. at which time the theoretical hydrogen uptake had been achieved. The reaction mixture was filtered and the filtrate was concentrated. The residue was dissolved in $CH_2Cl_2$ (250 ml) and triphosgene (6.3 g; 0.06447 mole) dissolved in 25 ml $CH_2Cl_2$ was added. The reaction was exothermic. The reaction mixture was stirred for 1 hr. then concentrated. The solid was triturated with water and filtered, washed with $Et_2O$ and suction dried. 9.9 g (76%) of a purple-white solid.

$C_{11}H_{14}N_2O_2$ * 0.1 $H_2O$ M.W. 208.05.

| Elements | Calc | Found |
|---|---|---|
| Carbon | 63.51 | 63.31 |
| Hydrogen | 6.88 | 6.93 |
| Nitrogen | 13.46 | 13.42 |

The benzimidazolone compounds of Examples 26 and 28 can be used to prepare the compounds of the claimed invention in a manner similar to that of Examples 12–24.

EXAMPLE 29

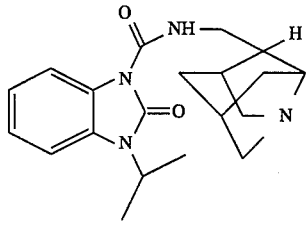

N-[(Hexahydro-2β,6β-methano-1H,
7aα-pyrrolizin-1β-yl)methyl
]2,3-dihydro-3-(1-methylethyl)-2-oxo-1H-
benzimidazole-1-carboxamide 60% NaH/Mineral oil (80 mg; 0.002 mole) was washed with hexane and suspended in THF. 1-isopropyl-2-benzimidazolinone (176 mg; 0.002 mole) was added to the suspension. This mixture was stirred 15 minutes before adding to a mixture of 2.5 ml (0.004 mole) 20% phosgene/2.5 ml THF. The resulting mixture was filtered through celite and concentrated. The residue was redissolved in THF (5.0 ml) and. the amine of example 11G (76 mg; 0.0005 mole) was added with 0.5 ml of $Et_3N$. This mixture was stirred 1 hour, filtered and the filtrate concentrated, The residue was chromatographed on a prep tlc plate, eluting with 10% MeOH/$CHCl_3$/0.25 $NH_4OH$. The product was washed from the silica with 5% $NH_4OH$/MeOH. The filtrate was concentrated and the residue was redissolved in $CHCl_3$ and filtered through celite and concentrated. 41 mg (24%) of product was isolated. The product was converted to the HCl salt by dissolving 26 µl of acetyl chloride in 5.0 ml of MeOH and adding this solution to the product, then concentrating to dryness.

$C_{20}H_{26}N_4O_2$ ·1 HCl ·1.5 $H_2O$ M.W. 417.94.

| Elements | Calc | Found |
|---|---|---|
| Carbon | 59.77 | 59.59 |
| Hydrogen | 7.52 | 7.41 |
| Nitrogen | 13.94 | 13.56 |
| Chlorine | 8.82 | 8.48 |

EXAMPLE 30

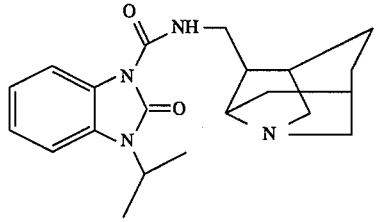

N-[(Hexahydro-2β,6β-methano-1H,
7aα-pyrrolizin-1α-yl)methyl
]2,3-dihydro-3-(1-methylethyl)-2-oxo-1H-
benzimidazole-1-carboxamide 60% NaH/Mineral oil (80 mg; 0.002 mole) was washed with hexane and suspended in THF. 1-isopropyl-2-benzimidazolinone (176 mg; 0.002 mole) was added to the suspension. This mixture was stirred 15 minutes before adding to a mixture of 2.5 ml (0.004 mole) 20% phosgene/2.5 ml THF. The resulting mixture was filtered through celite and concentrated. The residue was redissolved in THF (5.0 ml) and the amine of example 11F (76 mg; 0.0005 mole) was added with 0.5 ml of Et₃N. This mixture was stirred 1 hour, filtered and the filtrate concentrated. The residue was chromatographed on a prep tlc plate, eluting with 10% MeOH/CHCl₃/ 0.25 NH₄OH. The product was washed from the silica with 5% NH₄OH/MeOH. The filtrate was concentrated and the residue was redissolved in CHCl₃ and filtered through celite and concentrated. 51 mg (30%) of product was isolated. The product was converted to the HCl salt by dissolving 26 μl of acetyl chloride in 5.0 ml of MeOH and adding this solution to the product, then concentrating to dryness.

$C_{20}H_{26}N_4O_2 \cdot 1.2$ HCl $\cdot 1.75$ $H_2O$ M. W. 429.45.

| Elements | Calc | Found |
| --- | --- | --- |
| Carbon | 55.90 | 55.92 |
| Hydrogen | 7.20 | 6.81 |
| Nitrogen | 13.04 | 12.78 |
| Chlorine | 9.90 | 9.66 |

EXAMPLE 31A

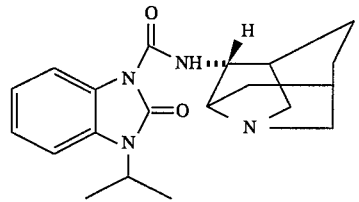

N-[(Hexahydro-2β,6β-methano-1H, 7aα-pyrrolizin-1α-yl]-2,3-dihydro-3 (1-methylethyl)-2-oxo-1H-benzimidazole-1-carboxamide.

EXAMPLE 31B

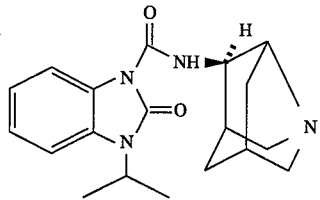

N-[(Hexahydro-2β,6β-methano-1H, 7aα-pyrrolizin-1β-yl]-2,3-dihydro-3 (1-methylethyl)-2-oxo-1H-benzimidazole-1-carboxamide 60% NaH/Mineral oil (80 mg; 0.002 mole) was washed with hexane and suspended in THF. 1-isopropyl-2-benzimidazolinone (128 mg; 0.0005 mole) was added to the suspension. This mixture was stirred 15 minutes before adding to a mixture of 2.5 ml (0.004 mole) 20% phosgene/2.5 ml THF. The resulting mixture was filtered through celite and concentrated. The residue was redissolved in THF (5.0 ml) and the amine of example 11H (76 mg; 0.0005 mole) was added with 0.5 ml of Et₃N. This mixture was stirred 1 hour, filtered and the filtrate concentrated. The residue was chromatographed on a prep tlc plate, eluting with 10% MeOH/ CHCl₃/0.25 NH₄OH. Two components were isolated The products were washed from the silica with 5% NH₄OH/ MeOH. The filtrates were concentrated and the residue was redissolved in CHCl₃ and filtered through celite and concentrated.

The first component: Example 31A; 4 mg (2.3%). The product was converted to the HCl salt by dissolving 6 μl of acetyl chloride in 5.0 ml of MeOH and adding this solution to the product, then concentrating to dryness.

$C_{19}H_{24}N_4O_2$; M.W. 340.425 High Resolution Mass Spec CMR 300 (CDCl₃) ¹³C:(ppm) 20.70, 29.62, 35.43, 36.29, 39.34, 46.35, 57.37, 62.09, 63..91, 67.10, 109.77, 116.22, 123.25, 124.35, 124.32, 128.44, 151.97, 153.77.

The second component: Example 31B; 51 mg (30%) of product was isolated. The product was converted to the HCl salt by dissolving 16 ml of acetyl chloride in 5.0 of MeOH and adding this solution to the product, then concentrating to dryness.

$C_{19}H_{24}N_4O_2$; M.W. 340.425 High Resolution Mass Spec CMR 300 (CDCl₃) ¹³C:(ppm) 20.63, 33.49, 36.42, 41.84, 42.36, 46.45, 63.38, 63.51, 66.74, 68.96, 109.66, 116.10, 123.18, 124.30, 149.45, 153.23.

EXAMPLE 32

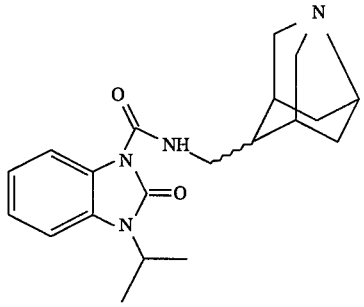

N-(Hexahydro-2,6-methano-1H-pyrrolizin-8-ylmethyl]-2,3-dihydro-3 (1-methylethyl)-2-oxo-1H-benzimidazole-1-carboxamide A 60% NaH/mineral oil dispersion was washed with hexane and suspended in THF (20 mL). 1-isopropyl-1,3-dihydro-2H-benzimidazol-2-one (243 mg, 1.38 mmol) was added to the suspension. This mixture was stirred for 15 minutes before adding it to a mixture of 5.4 mL (11.0 mmol) of 20% phosgene (toluene)/5.4 mL THF. The resulting mixture was stirred for 2.5 hours, filtered through celite, and concentrated. The residue was redissolved in THF (2.0 mL) and the amine of Example 11D (210 mg; 1.38 mmol) was added with triethylamine (0.290 mL, 2.1 mmol). This mixture was stirred for 18 hours and then concentrated to dryness. The :residue was dissolved in chloroform, washed with saturated aqueous K₂CO₃, water, and then dried over K₂CO₃. Filtration and concentration afforded an oil. Purification by chromatography on silica gel eluting with 5% methanol(NH₃)/chloroform gave 114 mg (23%) of the title compound.

Anal. calc'd for $C_{20}H_{26}N_4O_2 \cdot 1.5$ $H_2O$: C, 65.28; H, 7.53; N, 5.23. Found: C, 65.12; H, 7.63; N, 14.96. MS, calc'd for $C_{20}H_{26}N_4O_2$: 355.2056. Found: 355.2046.

EXAMPLE 33

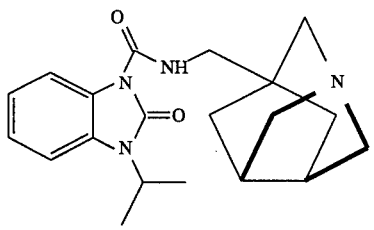

N-[(Hexahydro-2,5β-methano-1H-3aα,6aα-cyclopenta-[c]pyrrol-5-yl)methyl]-2,3-dihydro 3-(1-methylethyl)-2-oxo-1H-benzimidazole-1-carboxamide Following the procedure of Example 12, 1-(methylethyl)-1,3-dihydro-2H-benzimidazol-2-one was reacted with the amine of Example 11e to afford the title compound in 40% yield. 1H NMR (300 MHz, CDCl$_3$) δ1.58 (d, 6H); 1.78 (m, 4H); 2.68 (m, 2H); 2.82 (dd, 2H); 2.91 (s, 2H); 2.96 (m, 2H); 3.28 (d, 2H); 4.69 (quint, 1H); 7.17 (m, 3H), 8.25 (d, 1H); 8.84 (t, 1H).

EXAMPLE 34

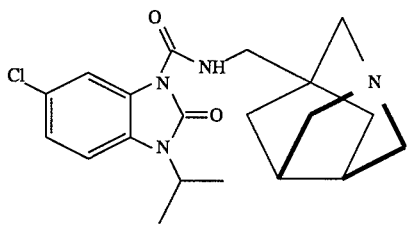

N-[(Hexahydro-2,5β-methano-1H-3aα,6aα-cyclopenta[c]-pyrrol-5-yl) methyl]-6-chloro-2,3-dihydro-3-(1-methylethyl)-2-oxo-1-benzimidazole-1-carboxamide Following the procedure of Example 12, 5-chloro-1-(methylethyl) 1,3-dihydro-2H-benzimidazol-2-one was reacted with the amine of Example 11E to afford the title compound in 40% yield. 1H NMR (300 MHz, CDCl$_3$) δ 1.58 (d, 6H); 1.78 (m, 4H); 2.68 (m, 2H); 2.82 (dd, 2H); 2.91 (s, 2H); 2.96 (m, 2H); 3.28 (d, 2H); 4.69 (quint, 1H); 7.11 (d, 1H), 7.18 (dd, 1H); 8.23 (d, 1H); 8.84 (t, 1H).

EXAMPLE 35

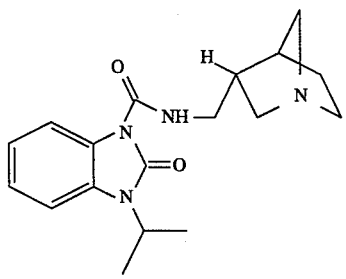

N-[(endo-1-azabicyclo[2.2.1]heptan-3-yl )methyl-]-2,3-dihydro-3-(1-methylethyl)-2-oxo-1H-benzimidazole-1-carboxamide Sodium hydride (60% dispersion in oil, 91 mg, 2.27 mmole) was washed with hexane (4 mL) and then slurried in THF (3 mL). The solid 3-isopropylbenzimidazolone (200 mg, 1.14 mmol) was added in one portion and the mixture was stirred 5 minutes until no further H$_2$ evolution was noted. The solution was tranferred via cannula to a solution of 1.18 ml phosgene in toluene (1.93 M, 2.27 mmol) in THF (2 mL). The mixture was stirred for 10 minutes before filtering to remove the sodium chloride precipitate. The sodium chloride was washed with THF and the combined THF solution was evaporated in vacuo. The residue was redissolved in THF (5 mL) and added via cannula to a solution of endo-3-aminomethyl-1-azabicyclo [2.2.1]heptane of example 11L (143 mg, 1.14 mmol). The mixture was stirred for 18 hours whereupon the THF was removed in vacuo. The residue was taken up into saturated aqueous K$_2$CO$_3$ (10 mL) and extracted with chloroform (4×10 mL). The combined extracts were dried (Na$_2$SO$_4$), filtered and concentrated in vacuo to give a residue (380 mg). The residue was purified via preparative silica gel TLC (eluted with 90:10:1 CHCl$_3$/CH$_3$OH/NH$_4$OH) to give 149 mg (40%) endo-product freebase and 5 mg (1%) exo-product freebase. The endo-freebase product (136 mg, 0.42 mmol) was dissolved in CH$_3$OH (2 mL) and 1.0 N HCl in methanol (0.457 mL) was added. Diethyl ether was added to precipitate the resulting hydrochloride salt. The salt was filtered, washed with ether and dried to give the hydrochloride salt (116 mg).

$^1$H NMR (DMSO-d$_6$) δ 10.9 (br s, 1H), 8.97 (m, 1H, NH), 8.06 (d, J=8 Hz, 1H), 7.42 (d, J=8 Hz, 1H), 7.21 (t, J=8 Hz, 1H), 7.13 (t, J=8 Hz, 1H), 4.64 (heptet, J=7 Hz, 1H), 3.41 (m, 1H), 3.32–3.20 (4 H), 3.11 (m, 1H), 3.04 (m, 2 H), 2.73 (d, J=4 Hz, 1H), 2.27 (m, 1H), 1.96 1H), 1.58 (m, 1H), 1.49 (d, J=7 Hz, 6H). $^{13}$C NMR (DMSO-d$_6$) δ151.8, 151.4, 127.7, 126.1, 123.4, 121.8, 114.2, 109.4, 55.8, 55.4, 51.2, 44.9, 41.3, 40.1, 37.9, 27.2, 19.4. MS (El) m/z 328 (M, 16), 215 (21), 176 (75), 161 (22), 153 (33), 134 (100), 110 (48), 96 (64), 91 (22), 57 (38). Anal. (C$_{18}$H$_{24}$N$_4$O$_2$+1.0 HCl+1.2 H$_2$O) C, H, N, Cl. HPLC analysis 100% endo. DSC m.p. 211.8° C.

EXAMPLE 36

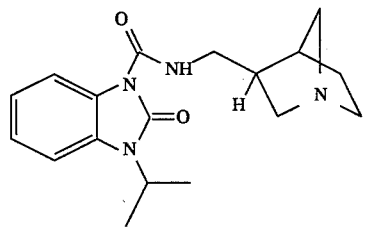

N-[(exo-1-azabicyclo[2.2.1]heptan-3-yl)methyl-]-2,3-dihydro-3-(1-methylethyl) 2-oxo-1H-benzimidazole-1-carboxamide Sodium hydride (60% dispersion in oil, 91 mg, 2.27 mmole) was washed with hexane (5 mL) and then slurried in THF (3 mL). The solid 3-isopropylbenzimidazolone (200 mg, 1.14 mmol) was added in one portion and the mixture was stirred 5 minutes until no further H$_2$ evolution was noted. The solution was transferred via cannula to a solution of 1.18 ml phosgene in toluene (1.93 M, 2.27 mmol) in THF (3 mL). The mixture was stirred for 10 minutes before filtering to remove the sodium chloride precipitate. The sodium chloride was washed with THF and the combined THF solution was evaporated in vacuo. The residue was redissolved in THF (5 mL) and added via cannula to a solution of endo-3-aminomethyl-1-azabicyclo[2.2.1]heptane of example 11K (143 mg, 1.14 mmol). The mixture was stirred for 3.5 hours whereupon the THF was removed in vacuo. The residue was taken up into saturated aqueous $K_2CO_3$ (10 mL) and extracted with chloroform (4×10 mL). The combined extracts were dried ($Na_2SO_4$), filtered and concentrated in vacuo to give a residue (318 mg). The residue was purified via preparative silica gel TLC (eluted with 90:10:1 $CHCl_3/CH_3OH/NH_4OH$) to give 144 mg of a ca. 90:10 exo/endo mixture of products, as judged by $^{13}C$ NMR analysis. A second preparative silica gel TLC separation (eluted with 93:7:1 $CHCl_3/CH_3OH/NH_4OH$) was performed to give 110 mg of exo-free base product. The exo-free base product (108 mg, 0.33 mmol) was dissolved in $CH_3OH$ (2 mL) and 1.0 N HCl in methanol (0.361 mL) was added. Diethyl ether was added to precipitate the resulting hydrochloride salt. The salt was filtered, washed with ether and dried to give 99 mg hydrochloride salt.

$^1H$ NMR (DMSO-$d_6$) δ 10.7 (br s, 1H), 8.83 (m, 1H, NH), 8.05 (d, J=8 Hz, 1H), 7.42 (d, J=8 Hz, 1H), 7.21 (t, J=8 Hz, 1H), 7.13 (t, J=8 Hz, 1H), 4.64 (heptet, J=7 Hz, 1H), 3.47–3.40 (m, 2H), 3.20 (m, 2H) 3.11 (m, 1H), 2.87–2.81 (m, 2H), 2.68 (m, 1H), 2.49 (m, 1H), 2.02 (m, 1H), 1.88 (m, 1H) 1.49 (d, J= 7 Hz, 6H). $^{13}C$ NMR (DMSO-$d_6$) δ151.8, 151.1, 127.7, 126.1, 123.4, 121.8, 114.2, 109.4, 59.2, 54.6, 51.7, 45.0, 39.5, 38.0, 37.7, 20.9, 19.4. MS (El) m/z 328 (M, 52), 176 (100), 161 (22), 153 (46), 134 (86), 110 (26), 96 (55), 57 (25). Anal. ($C_{18}H_{24}N_4O_2$+1.0 HCl+0.3 $H_2O$) C, H, N, Cl. HPLC analysis 99.5% exo. DSC m.p. 248.1° C.

Bezold-Jarisch Reflex

The compound to be evaluated was administered i.p. (mg/kg) to a group of 3 mice. Thirty minutes later, a 5-HT (0.25 mg/kg i.v.)-induced bradycardia was recorded in pentobarbital anesthetized animals. A greater than 50 percent (>50) reduction in the bradycardic response relative to vehicle-treated control mice was considered significant.

This method has been described by Saxena, P. R. and Lawang, A., Arch. Int. Pharmacodyn., 277:235–252, 1985.

The assay results for the compounds of the present invention and their Minimum Effective Dose (MED) and the reference compounds and their MEDs are recorded in Table I.

TABLE I

| COMPOUND | Minimum Effective Dose (MED) mg/kg |
|---|---|
| Example 13 | 10 |
| Example 23 | 1 |
| BRL-43694 | 0.05 |
| cisapride | 5 |
| cyproheptadine | 5 |
| domperidone | >10 |
| GR-38032 | 0.5 |
| ketanserin | >10 |
| mecamylamine | 2.5 |
| methylsergide | >10 |
| metoclopramide | 5 |
| scopolamine | 2.5 |

Serotonin (5-HT$_3$)

Procedure

GR65630 binds to the 5-HT$_3$ receptor. Brain cortices were obtained from male rats and a membrane fraction prepared by standard techniques. 0.04 mg of membrane prep was incubated with 0.2 nM [$^3H$]-GR656630 for 60 minutes at 22° C. Non-specific binding was estimated in the presence of 1 uM ICS 205–930. Membranes were filtered and washed times and the filters were counted to determine [3H]-GR65630 specifically bound. Kilpatrick G. J., Jones B. J. and Tyers M. B. Identification and distribution of 5-HT$_3$ receptors in rat brain using radioligand binding assay. Nature, 330 : 746–748, 1987.

Results

Kd=2.46 nM
Bmax=154 fmol/mg protein
% Specific Binding: 70

TABLE II

| Effect of Compounds on [H]-GR65630 Bound (0.2 nM) | |
|---|---|
| Compound | Ki |
| Quipazine | 0.18 nM |
| ICS 205-930 | 0.51 nM |
| 5-HT | 0.39 uM |
| RU24969 | 1.85 uM |
| Zacopride | 0.18 nM |
| Example 12 | 2,800 nM |
| Example 13 | 120 nM |
| Example 14 | 36 nM |
| Example 15 | 92 nM |
| Example 16 | 1,200 nM |
| Example 17 | 41% @ 10,000 nM |
| Example 18 | 1,200 nM |
| Example 19 | 1,200 nM |
| Example 20 | 19 nM |
| Example 21 | 55 nM |
| Example 22 | 360 nM |
| Example 22B | 4.9 nM |
| Example 23 | 75 nM |
| Example 24 | 2.0 nM |

In Vitro Functional Assay for Serotonin 5-HT$_4$ agonism: RAT TMM

Serotonin 5-HT$_4$ agonism was measured in the rat esophagus in vitro preparation as reported by Baxter et al (Naunyn. Schmied. Arch. Pharmacol. 1991, 343, 439). Agonist activity was determined utilizing relaxation of carbachol-contracted rat tunica muscularis mucosae. One 2 cm segment of intrathoracic esophagus proximal to the diaphragm was removed from male rats, weighing approximately 300 gm, and the outer muscle layers removed. The inner tunica muscularis mucosa was mounted under 0.2–0.3 g of tension in a tissue bath containing oxygenated Tyrode's solution at 37° C. Cortisterone acetate (30 μM) and fluoxetine (1 μM) were included in the buffer to prevent uptake of serotonin, as well as pargyline (10 μM) to inhibit monoamine oxidase. Following a 30 min equilibrium period, tissues were isometrically contracted with carbachol (3 μM) to obtain a tonic contraction. A stable plateau was obtained within 20 min when test compound was added cumulatively to relax the muscle strip. EC50 values were obtained for each agonist in tissues from 5 rats. EC50 values for agonists at this 5-HT$_4$ receptor are indicated in Table III.

TABLE III

| Compound | 5-HT$_4$ Agonism (Rat TMM) In Vitro Assay: EC50 Values |
|---|---|
| Serotonin | 9 nM |
| Example 12 | 9467 nM |
| Example 12A | 1361 nM |
| Example 12B | 374 nM |
| Example 13 | 179 nM |
| Example 14 | 3833 nM |
| Example 14A | 874 nM |
| Example 15 | 4584 nM |
| Example 16 | 10000 nM |
| Example 19B | 926 nM |
| Example 20 | 10000 nM |
| Example 21 | 2135 nM |
| Example 22C | 722 nM |
| Example 23 | 374 nM |
| Example 24 | 1506 nM |
| Example 29 | 1634 nM |
| Example 30 | 219 nM |
| Example 32 | 1319 nM |
| Example 33 | 337 nM |
| Example 34 | 248 nM |
| Example 35 | 294 nM |
| Example 36 | 302 nM |

Although this invention has been described with respect to specific embodiments, the details of these embodiments are not to be construed as limitations.

What is claimed is:

1. A compound of the formula

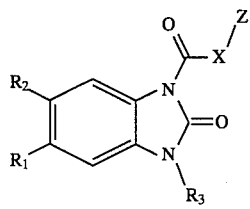

or a pharmaceutically acceptable salt thereof
wherein $R_1$ and $R_2$ are independently selected from the group consisting of hydrogen, $C_1-C_{12}$-alkoxy, halogen, amino, mono-$C_1-C_{12}$-alkylamino, di-$C_1-C_{12}$-alkylamino, acylamino of the formula

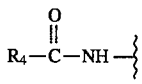

with $R_4$ being $C_1-C_{12}$-alkyl, and $C_1-C_{12}$-alkylsulfonylamino;

$R_3$ is selected from the group consisting of H, $C_1-C_{12}$-alkyl and $C_3-C_6$-cycloalkyl;

X is NH or O;

Z is selected from the group consisting of

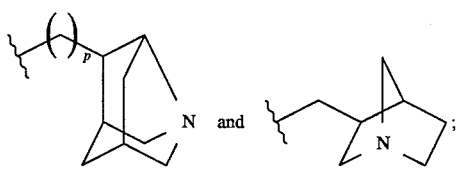

and p is 0 or 1.

2. A pharmaceutical composition comprising a therapeutically effective amount of a compound of claim 1 of the formula

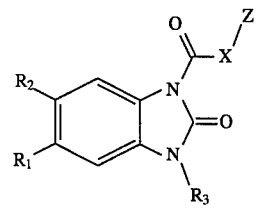

or a pharmaceutically acceptable salt thereof wherein $R_1$ and $R_2$ are independently selected from the group consisting of hydrogen, $C_1-C_{12}$-alkoxy, halogen, amino, mono-$C_1-C_{12}$-alkylamino, di-$C_1-C_{12}$-alkylamino, acylamino of the formula

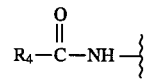

with $R_4$ being $C_1-C_{12}$-alkyl, and $C_1-C_{12}$-alkylsulfonylamino;

$R_3$ is selected from the group consisting of H, $C_1-C_{12}$-alkyl and $C_3-C_6$-cycloalkyl X is NH or O;

Z is selected from the group consisting of

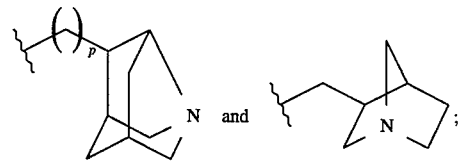

and a pharmaceutically acceptable carrier.

3. A pharmaceutical composition according to claim 2 wherein the compound is selected from the group consisting of N-(Hexahydro-2,6-methano-1H-pyrrolizin-1-ylmethyl)-2,3-dihydro-3-(1-methylethyl) 2-oxo- 1H-benzimidazole-1-carboxamide;

N-[(endo-1-azabicyclo[2.2.1]heptan-3-yl)methyl]-2,3-dihydro-3-(1-methylethyl) 2-oxo-1H-benzimidazole-1carboxamide;

N-[(exo-1-azabicyclo[2.2.1]heptan-3-yl)methyl]-2,3-dihydro-3-(1-methylethyl) 2-oxo-1H-benzimidazole-1-carboxamide;

N-[(Hexahydro-2β,6β-methano-1H,7aα-pyrrolizin-1β-yl)methyl]-2,3-dihydro-3 (1-methylethyl)-2-oxo-1H-benzimidazole-1-carboxamide;

N-[(Hexahydro-2β,6β-methano-1H,7aα-pyyrrolizin-1α-yl)methyl]-2,3-dihydro-3 (1-methylethyl)-2-oxo-1H-benzimidazole-1-carboxamide;

N-[(Hexahydro-2β,6β-methano-1H,7aα-pyrrolizin-1α-yl)-2,3-dihydro-3 (1-methylethyl)-2-oxo-1H-benzimidazole-1-carboxamide; and N-[(Hexahydro-2β,6β-methano-1H,7aα-pyrrolizin-1β-yl)-2,3-dihydro-3 (1-methylethyl)-2-oxo-1H-benzimidazole-1-carboxamide.

4. A compound according to claim 1 wherein Z is

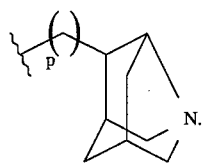

5. A compound according to claim 4 wherein the compound is selected from the group consisting of N-[(hexahydro-2β,6β-methano-1H, 7aα-pyrrolizin-1α-yl)methyl]-2,3-dihydro-3-(1-methylethyl)-2-oxo-1H benzimidazole-1-carboxamide;
N-[(hexahydro-2β,6β-methano-1H, 7aα-pyrrolizin-1α-yl)-2,3-dihydro-3-(1-methylethyl) 2-oxo-1H-benzimidazole-1-carboxamide;
N-[(Hexahydro-2β,6β-methano-1H, 7aα-pyrrolizin-1β-yl)-2,3-dihydro-3-(1-methylethyl) 2-oxo-1H-benzimidazole-1-carboxamide; and benzimidazole-1-carboxamide; and N-(Hexahydro-2,6-methano-1H-pyrrolizin-1-ylmethyl)-2,3-dihydro-3-(1-methylethyl) 2-oxo-1H-benzimidazole-1-carboxamide.

6. A compound according to claim 1 wherein Z is

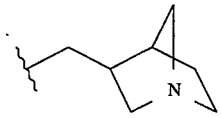

7. A compound according to claim 6 wherein the compound is selected from the group consisting of N-[(endo-1-azabicyclo [2.2.1]heptan-3-yl) methyl-]-2,3-dihydro-3-(1-methylethyl) 2-oxo-1H-benzimidazole-1-carboxamide; and N-[(exo-1-azabicyclo[2.2.1]heptan-3-yl)methyl-]-2,3-dihydro-3-(1-methylethyl) 2-oxo-1H-benzimidazole-1-carboxamide.

* * * * *